(12) United States Patent
Sims et al.

(10) Patent No.: US 10,973,567 B2
(45) Date of Patent: Apr. 13, 2021

(54) ELECTROSURGICAL FORCEPS FOR GRASPING, TREATING, AND/OR DIVIDING TISSUE

(71) Applicant: COVIDIEN LP, Mansfield, MA (US)

(72) Inventors: Grant T. Sims, Boulder, CO (US);
Benjamin R. Arts, Lafayette, CO (US);
Kelley D. Goodman, Erie, CO (US);
David Michael Keffeler, Niwot, CO (US); Craig V. Krastins, Arvada, CO (US); Jennifer E. Lee, Boulder, CO (US); Robert F. McCullough, Jr., Boulder, CO (US); Daniel W. Mercier, Erie, CO (US)

(73) Assignee: Covidien LP, Mansfield, MA (US)

( * ) Notice: Subject to any disclaimer, the term of this patent is extended or adjusted under 35 U.S.C. 154(b) by 910 days.

(21) Appl. No.: 15/593,672

(22) Filed: May 12, 2017

(65) Prior Publication Data
US 2018/0325580 A1    Nov. 15, 2018

(51) Int. Cl.
*A61B 18/14* (2006.01)
*A61B 18/12* (2006.01)
(Continued)

(52) U.S. Cl.
CPC .......... *A61B 18/1445* (2013.01); *A61B 18/12* (2013.01); *A61B 18/1233* (2013.01);
(Continued)

(58) Field of Classification Search
CPC ........ A61B 18/1445; A61B 2018/1455; A61B 18/12; A61B 18/1442; A61B 2018/00172;
(Continued)

(56) References Cited

U.S. PATENT DOCUMENTS

D249,549 S    9/1978    Pike
D263,020 S    2/1982    Rau, III
(Continued)

FOREIGN PATENT DOCUMENTS

CN    201299462        9/2009
CN    202086577 U    12/2011
(Continued)

OTHER PUBLICATIONS

Extended European Search Report issued in corresponding application No. 18171773.7 dated Oct. 8, 2018, 7 pages.
(Continued)

*Primary Examiner* — Daniel W Fowler
*Assistant Examiner* — Tigist D Demie
(74) *Attorney, Agent, or Firm* — Carter, DeLuca & Farrell LLP

(57) ABSTRACT

An electrosurgical forceps includes first and second shaft members pivotably coupled to one another via a pivot member such that pivoting of the first and second shaft members between spaced-apart and approximated positions pivots jaw members thereof between open and closed positions. A knife is translatable between retracted and extended positions. A knife deployment mechanism is operably coupled to the first shaft member and includes at least one trigger and at least one linkage coupling the at least one trigger with the knife such that pivoting of the at least one trigger relative to the first shaft member translates the knife between the retracted and extended positions. A knife lockout biased towards a locked position inhibits distal translation of the knife. The knife lockout is movable from the locked position to an unlocked position upon approximation of the jaw members to permit distal translation of the knife.

20 Claims, 19 Drawing Sheets

(51) Int. Cl.
*A61B 90/00* (2016.01)
*A61B 18/00* (2006.01)

(52) U.S. Cl.
CPC .............. *A61B 2018/00297* (2013.01); *A61B 2018/00601* (2013.01); *A61B 2018/146* (2013.01); *A61B 2018/1412* (2013.01); *A61B 2018/1455* (2013.01); *A61B 2090/034* (2016.02)

(58) Field of Classification Search
CPC ........... A61B 2018/00178; A61B 2018/00297; A61B 2018/1412; A61B 2090/034
See application file for complete search history.

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| 4,763,669 A | 8/1988 | Jaeger |
| D298,353 S | 11/1988 | Manno |
| D299,413 S | 1/1989 | DeCarolis |
| 5,100,420 A | 3/1992 | Green et al. |
| 5,258,001 A | 11/1993 | Corman |
| D343,453 S | 1/1994 | Noda |
| 5,304,203 A | 4/1994 | El-Mallawany et al. |
| D348,930 S | 7/1994 | Olson |
| D349,341 S | 8/1994 | Lichtman et al. |
| 5,344,424 A | 9/1994 | Roberts et al. |
| D354,564 S | 1/1995 | Medema |
| D358,887 S | 5/1995 | Feinberg |
| 5,540,685 A | 7/1996 | Parins et al. |
| 5,578,052 A | 11/1996 | Koros et al. |
| 5,611,808 A | 3/1997 | Hossain et al. |
| 5,618,294 A | 4/1997 | Aust et al. |
| D384,413 S | 9/1997 | Zlock et al. |
| 5,665,100 A | 9/1997 | Yoon |
| 5,752,644 A | 5/1998 | Bolanos et al. |
| H001745 H | 8/1998 | Paraschac |
| 5,814,043 A | 9/1998 | Shapeton |
| D402,028 S | 12/1998 | Grimm et al. |
| D408,018 S | 4/1999 | McNaughton |
| 5,913,874 A | 6/1999 | Berns et al. |
| 5,960,544 A | 10/1999 | Beyers |
| D416,089 S | 11/1999 | Barton et al. |
| 6,050,996 A | 4/2000 | Schmaltz et al. |
| D424,694 S | 5/2000 | Tetzlaff et al. |
| D425,201 S | 5/2000 | Tetzlaff et al. |
| H001904 H | 10/2000 | Yates et al. |
| 6,293,954 B1 | 9/2001 | Fogarty et al. |
| D449,886 S | 10/2001 | Tetzlaff et al. |
| 6,329,778 B1 | 12/2001 | Culp et al. |
| 6,334,861 B1 | 1/2002 | Chandler et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| 6,406,485 B1 | 6/2002 | Hossain et al. |
| H002037 H | 7/2002 | Yates et al. |
| 6,464,704 B2 | 10/2002 | Schmaltz et al. |
| D465,281 S | 11/2002 | Lang |
| D466,209 S | 11/2002 | Bon |
| 6,511,480 B1 | 1/2003 | Tetzlaff et al. |
| 6,673,092 B1 | 1/2004 | Bacher |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| 7,118,570 B2 | 10/2006 | Tetzlaff et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| 7,329,257 B2 | 2/2008 | Kanehira et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,431,730 B2 | 10/2008 | Viola |
| D582,038 S | 12/2008 | Swoyer et al. |
| 7,641,653 B2 | 1/2010 | Dalla Betta et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| 7,854,185 B2 | 12/2010 | Zhang et al. |
| D630,324 S | 1/2011 | Reschke |
| 7,896,878 B2 | 3/2011 | Johnson et al. |
| D649,249 S | 11/2011 | Guerra |
| D649,643 S | 11/2011 | Allen, IV et al. |
| 8,147,489 B2 | 4/2012 | Moses et al. |
| D661,394 S | 6/2012 | Romero et al. |
| 8,298,233 B2 | 10/2012 | Mueller |
| D670,808 S | 11/2012 | Moua et al. |
| 8,366,709 B2 | 2/2013 | Schechter et al. |
| 8,394,096 B2 | 3/2013 | Moses et al. |
| D680,220 S | 4/2013 | Rachlin |
| 8,409,246 B2 | 4/2013 | Kerr et al. |
| 8,409,247 B2 | 4/2013 | Garrison et al. |
| 8,425,504 B2 | 4/2013 | Orton et al. |
| 8,425,511 B2 | 4/2013 | Olson |
| 8,430,877 B2 | 4/2013 | Kerr et al. |
| 8,439,913 B2 | 5/2013 | Horner et al. |
| 8,469,716 B2 | 6/2013 | Fedotov et al. |
| 8,469,991 B2 | 6/2013 | Kerr |
| 8,469,992 B2 | 6/2013 | Roy et al. |
| 8,480,671 B2 | 7/2013 | Mueller |
| 8,491,624 B2 | 7/2013 | Kerr et al. |
| 8,491,625 B2 | 7/2013 | Horner |
| 8,491,626 B2 | 7/2013 | Roy et al. |
| 8,512,336 B2 | 8/2013 | Couture |
| 8,540,749 B2 | 9/2013 | Garrison et al. |
| 8,551,091 B2 | 10/2013 | Couture et al. |
| 8,556,929 B2 | 10/2013 | Harper et al. |
| 8,568,397 B2 | 10/2013 | Horner et al. |
| 8,568,408 B2 | 10/2013 | Townsend et al. |
| 8,585,736 B2 | 11/2013 | Horner et al. |
| 8,591,510 B2 | 11/2013 | Allen, IV et al. |
| 8,597,295 B2 | 12/2013 | Kerr |
| 8,623,018 B2 | 1/2014 | Horner et al. |
| 8,628,557 B2 | 1/2014 | Collings et al. |
| 8,641,712 B2 | 2/2014 | Couture |
| 8,647,343 B2 | 2/2014 | Chojin et al. |
| 8,652,135 B2 | 2/2014 | Nau, Jr. |
| 8,663,222 B2 | 3/2014 | Anderson et al. |
| 8,672,939 B2 | 3/2014 | Garrison |
| 8,679,098 B2 | 3/2014 | Hart |
| 8,685,009 B2 | 4/2014 | Chernov et al. |
| 8,685,021 B2 | 4/2014 | Chernov et al. |
| 8,685,056 B2 | 4/2014 | Evans et al. |
| 8,702,737 B2 | 4/2014 | Chojin et al. |
| 8,702,749 B2 | 4/2014 | Twomey |
| 8,734,445 B2 | 5/2014 | Johnson et al. |
| 8,740,898 B2 | 6/2014 | Chojin et al. |
| 8,745,840 B2 | 6/2014 | Hempstead et al. |
| 8,747,434 B2 | 6/2014 | Larson et al. |
| 8,756,785 B2 | 6/2014 | Allen, IV et al. |
| 8,784,418 B2 | 7/2014 | Romero |
| 8,795,269 B2 | 8/2014 | Garrison |
| 8,808,288 B2 | 8/2014 | Reschke |
| 8,814,864 B2 | 8/2014 | Gilbert |

(56) References Cited

U.S. PATENT DOCUMENTS

| | | |
|---|---|---|
| 8,840,639 B2 | 9/2014 | Gerhardt, Jr. et al. |
| 8,845,636 B2 | 9/2014 | Allen, IV et al. |
| 8,852,185 B2 | 10/2014 | Twomey |
| 8,852,228 B2 | 10/2014 | Nau, Jr. |
| 8,858,553 B2 | 10/2014 | Chojin |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,888,775 B2 | 11/2014 | Nau, Jr. et al. |
| 8,898,888 B2 | 12/2014 | Brandt et al. |
| 8,900,232 B2 | 12/2014 | Ourada |
| 8,906,018 B2 | 12/2014 | Rooks et al. |
| 8,920,421 B2 | 12/2014 | Rupp |
| 8,932,293 B2 | 1/2015 | Chernov et al. |
| 8,936,614 B2 | 1/2015 | Allen, IV |
| 8,939,972 B2 | 1/2015 | Twomey |
| 8,945,175 B2 | 2/2015 | Twomey |
| 8,961,504 B2 | 2/2015 | Hoarau et al. |
| 8,968,283 B2 | 3/2015 | Kharin |
| 8,968,305 B2 | 3/2015 | Dumbauld et al. |
| 8,968,316 B2 | 3/2015 | Roy et al. |
| 8,968,357 B2 | 3/2015 | Mueller |
| 8,968,359 B2 | 3/2015 | Kerr et al. |
| 9,005,200 B2 | 4/2015 | Roy et al. |
| 9,017,372 B2 | 4/2015 | Artale et al. |
| 9,028,484 B2 | 5/2015 | Craig |
| 9,028,492 B2 | 5/2015 | Kerr et al. |
| 9,028,495 B2 | 5/2015 | Mueller et al. |
| 9,039,704 B2 | 5/2015 | Joseph |
| 9,039,732 B2 | 5/2015 | Sims et al. |
| 9,084,608 B2 | 7/2015 | Larson et al. |
| 9,113,933 B2 | 8/2015 | Chernova et al. |
| 9,113,934 B2 | 8/2015 | Chernov et al. |
| 9,161,807 B2 | 10/2015 | Garrison |
| 9,211,657 B2 | 12/2015 | Ackley et al. |
| 9,265,568 B2 | 2/2016 | Chernov et al. |
| 9,333,002 B2 | 5/2016 | Garrison |
| 9,381,059 B2 | 7/2016 | Garrison |
| 9,456,870 B2 | 10/2016 | Chernov et al. |
| 9,498,278 B2 | 11/2016 | Couture et al. |
| 9,498,279 B2 | 11/2016 | Artale et al. |
| 9,504,519 B2 | 11/2016 | Kerr et al. |
| 9,585,709 B2 | 3/2017 | Krapohl |
| 9,615,877 B2 | 4/2017 | Tyrrell et al. |
| 9,655,672 B2 | 5/2017 | Artale et al. |
| 2003/0018332 A1 | 1/2003 | Schmaltz et al. |
| 2003/0109875 A1 | 6/2003 | Tetzlaff et al. |
| 2003/0199869 A1 | 10/2003 | Johnson et al. |
| 2003/0220637 A1 | 11/2003 | Truckai et al. |
| 2003/0229344 A1 | 12/2003 | Dycus et al. |
| 2004/0092927 A1 | 5/2004 | Podhajsky et al. |
| 2004/0193153 A1* | 9/2004 | Sartor .............. A61B 18/1445 606/48 |
| 2005/0070889 A1 | 3/2005 | Nobis et al. |
| 2005/0107784 A1 | 5/2005 | Moses et al. |
| 2005/0113826 A1 | 5/2005 | Johnson et al. |
| 2005/0113828 A1 | 5/2005 | Shields et al. |
| 2005/0159745 A1 | 7/2005 | Truckai et al. |
| 2006/0253126 A1 | 11/2006 | Bjerken et al. |
| 2007/0062017 A1 | 3/2007 | Dycus et al. |
| 2007/0088356 A1 | 4/2007 | Moses et al. |
| 2007/0179499 A1 | 8/2007 | Garrison |
| 2007/0260241 A1 | 11/2007 | Dalla Betta et al. |
| 2008/0215048 A1 | 9/2008 | Hafner et al. |
| 2009/0131934 A1 | 5/2009 | Odom et al. |
| 2009/0171353 A1 | 7/2009 | Johnson et al. |
| 2009/0182327 A1 | 7/2009 | Unger |
| 2009/0240246 A1 | 9/2009 | Deville et al. |
| 2009/0302090 A1 | 12/2009 | Shah |
| 2009/0308909 A1 | 12/2009 | Nalagatla et al. |
| 2010/0016857 A1 | 1/2010 | McKenna et al. |
| 2010/0130977 A1 | 5/2010 | Garrison et al. |
| 2010/0179545 A1 | 7/2010 | Twomey et al. |
| 2010/0179547 A1 | 7/2010 | Cunningham et al. |
| 2010/0228250 A1 | 9/2010 | Brogna |
| 2010/0274244 A1 | 10/2010 | Heard |
| 2010/0292691 A1 | 11/2010 | Brogna |
| 2010/0305567 A1 | 12/2010 | Swanson |
| 2011/0054469 A1 | 3/2011 | Kappus et al. |
| 2011/0060314 A1 | 3/2011 | Wallace et al. |
| 2011/0060356 A1 | 3/2011 | Reschke et al. |
| 2011/0072638 A1 | 3/2011 | Brandt et al. |
| 2011/0087218 A1 | 4/2011 | Boudreaux et al. |
| 2011/0218530 A1 | 9/2011 | Reschke |
| 2011/0238065 A1 | 9/2011 | Hunt et al. |
| 2011/0238067 A1 | 9/2011 | Moses et al. |
| 2011/0257680 A1 | 10/2011 | Reschke et al. |
| 2011/0270245 A1 | 11/2011 | Horner et al. |
| 2011/0270251 A1 | 11/2011 | Horner et al. |
| 2011/0276049 A1 | 11/2011 | Gerhardt |
| 2011/0295313 A1 | 12/2011 | Kerr |
| 2012/0059372 A1 | 3/2012 | Johnson |
| 2012/0059409 A1 | 3/2012 | Reschke et al. |
| 2012/0083785 A1 | 4/2012 | Roy et al. |
| 2012/0083786 A1 | 4/2012 | Artale et al. |
| 2012/0083827 A1 | 4/2012 | Artale et al. |
| 2012/0123402 A1 | 5/2012 | Chernov et al. |
| 2012/0123404 A1 | 5/2012 | Craig |
| 2012/0123410 A1 | 5/2012 | Craig |
| 2012/0130367 A1 | 5/2012 | Garrison |
| 2012/0136354 A1 | 5/2012 | Rupp |
| 2012/0172868 A1 | 7/2012 | Twomey et al. |
| 2012/0172873 A1 | 7/2012 | Artale et al. |
| 2012/0172924 A1 | 7/2012 | Allen, IV |
| 2012/0184988 A1 | 7/2012 | Twomey et al. |
| 2012/0184989 A1 | 7/2012 | Twomey |
| 2012/0184990 A1 | 7/2012 | Twomey |
| 2012/0209263 A1 | 8/2012 | Sharp et al. |
| 2012/0215219 A1 | 8/2012 | Roy et al. |
| 2012/0239034 A1 | 9/2012 | Horner et al. |
| 2012/0253344 A1 | 10/2012 | Dumbauld et al. |
| 2012/0259331 A1 | 10/2012 | Garrison |
| 2012/0265241 A1 | 10/2012 | Hart et al. |
| 2012/0283727 A1 | 11/2012 | Twomey |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296317 A1 | 11/2012 | Chernov et al. |
| 2012/0296323 A1 | 11/2012 | Chernov et al. |
| 2012/0296324 A1 | 11/2012 | Chernov et al. |
| 2012/0296334 A1 | 11/2012 | Kharin |
| 2012/0303025 A1 | 11/2012 | Garrison |
| 2012/0323238 A1 | 12/2012 | Tyrrell et al. |
| 2012/0330308 A1 | 12/2012 | Joseph |
| 2012/0330309 A1 | 12/2012 | Joseph |
| 2013/0018364 A1 | 1/2013 | Chernov et al. |
| 2013/0018372 A1 | 1/2013 | Sims et al. |
| 2013/0018411 A1 | 1/2013 | Collings et al. |
| 2013/0022495 A1 | 1/2013 | Allen, IV et al. |
| 2013/0030432 A1 | 1/2013 | Garrison et al. |
| 2013/0000463 A1 | 2/2013 | Evans et al. |
| 2013/0041370 A1 | 2/2013 | Unger |
| 2013/0046295 A1 | 2/2013 | Kerr et al. |
| 2013/0046306 A1 | 2/2013 | Evans et al. |
| 2013/0046337 A1 | 2/2013 | Evans et al. |
| 2013/0060250 A1 | 3/2013 | Twomey et al. |
| 2013/0066318 A1 | 3/2013 | Kerr |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079762 A1 | 3/2013 | Twomey et al. |
| 2013/0079774 A1 | 3/2013 | Whitney et al. |
| 2013/0085491 A1 | 4/2013 | Twomey et al. |
| 2013/0085496 A1 | 4/2013 | Unger et al. |
| 2013/0103030 A1 | 4/2013 | Garrison |
| 2013/0103031 A1 | 4/2013 | Garrison |
| 2013/0103035 A1 | 4/2013 | Horner et al. |
| 2013/0123837 A1 | 5/2013 | Roy et al. |
| 2013/0138101 A1* | 5/2013 | Kerr .................. A61B 18/1442 606/45 |
| 2013/0138102 A1 | 5/2013 | Twomey et al. |
| 2013/0138129 A1 | 5/2013 | Garrison et al. |
| 2013/0144284 A1 | 6/2013 | Behnke, II et al. |

(56) References Cited

U.S. PATENT DOCUMENTS

| | | |
|---|---|---|
| 2013/0178852 A1 | 7/2013 | Allen, IV et al. |
| 2013/0185922 A1 | 7/2013 | Twomey et al. |
| 2013/0190753 A1 | 7/2013 | Garrison et al. |
| 2013/0190760 A1 | 7/2013 | Allen, IV et al. |
| 2013/0197503 A1 | 8/2013 | Orszulak |
| 2013/0226177 A1 | 8/2013 | Brandt et al. |
| 2014/0221994 A1 | 8/2014 | Reschke |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | McCullough, Jr. et al. |
| 2014/0257283 A1 | 9/2014 | Johnson et al. |
| 2014/0257284 A1 | 9/2014 | Artale |
| 2014/0257285 A1 | 9/2014 | Moua |
| 2014/0276803 A1 | 9/2014 | Hart |
| 2014/0284313 A1 | 9/2014 | Allen, IV et al. |
| 2014/0288549 A1 | 9/2014 | McKenna et al. |
| 2014/0288553 A1 | 9/2014 | Johnson et al. |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0066076 A1 | 3/2015 | Kerr et al. |
| 2015/0080889 A1 | 3/2015 | Cunningham et al. |
| 2015/0082928 A1 | 3/2015 | Kappus et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |
| 2016/0157922 A1* | 6/2016 | Lee ................ A61B 18/1442 606/51 |
| 2016/0157925 A1 | 6/2016 | Artale et al. |
| 2016/0175031 A1 | 6/2016 | Boudreaux |
| 2017/0020601 A1* | 1/2017 | Thomson ........... A61B 17/3201 |
| 2017/0128120 A1 | 5/2017 | Cho et al. |

FOREIGN PATENT DOCUMENTS

| | | |
|---|---|---|
| CN | 102525639 A | 7/2012 |
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 10031773 A1 | 11/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 1532932 A1 | 5/2005 |
| EP | 2301468 A1 | 3/2011 |
| EP | 2353535 A1 | 8/2011 |
| EP | 2436327 A1 | 4/2012 |
| EP | 2436330 A1 | 4/2012 |
| EP | 2529681 A1 | 12/2012 |
| EP | 3072467 A1 | 9/2016 |
| JP | 61-501068 | 9/1984 |
| JP | 11-47150 A | 6/1989 |
| JP | 6-502328 | 3/1992 |
| JP | 5-5106 | 1/1993 |
| JP | 05-40112 | 2/1993 |
| JP | 0006060945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | H07-265328 A | 10/1995 |
| JP | H08-56955 A | 3/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 09000538 A | 1/1997 |
| JP | H09-10223 A | 1/1997 |
| JP | 9-122138 A | 5/1997 |
| JP | 0010000195 A | 1/1998 |
| JP | H10-24051 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | H11-244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001-8944 | 1/2001 |
| JP | 2001008944 A | 1/2001 |
| JP | 2001-029355 A | 2/2001 |
| JP | 2001029356 A | 2/2001 |
| JP | 2001128990 A | 5/2001 |
| JP | 2001-190564 A | 7/2001 |
| JP | 2001-003400 | 11/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 10/1973 |
| WO | 94/00059 | 1/1994 |
| WO | 99-23933 A2 | 5/1999 |
| WO | 00/24330 | 5/2000 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/45589 A2 | 6/2002 |
| WO | 02080786 A1 | 10/2002 |
| WO | 02080793 A1 | 10/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |

(56) References Cited

FOREIGN PATENT DOCUMENTS

| WO | 2013/009758 A2 | 1/2013 |
|---|---|---|
| WO | 2013/022928 A1 | 2/2013 |
| WO | 2013134044 A1 | 9/2013 |
| WO | 2015017991 A1 | 2/2015 |

OTHER PUBLICATIONS

Canadian Office Action issued in Canadian Application No. 2,997,771 dated Jan. 4, 2019, 3 pages.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz, abandoned.
U.S. Appl. No. 09/591,328, filed Jun. 9, 2000, Thomas P. Ryan.
U.S. Appl. No. 12/336,970, filed Dec. 17, 2008, Paul R. Sremeich, abandoned.
U.S. Appl. No. 13/183,856, filed Jul. 15, 2011, John R. Twomey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument" Innovations That Work, .quadrature.Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 3, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicoletomy Using the LigaSure Vessel Sealing System" Innovations That Work,. quadrature.Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work,.quadrature. Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3.
Palazzo et al. "Randomized clinical trial of Ligasure versus open haemorrhoidectomy" British Journal of Surgery 2002, 39, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Seyfan et al. "Sutureless Closed Hemorrhoidectomy: A New Technique" Annals of Surgery vol. 234 No. 1, Jul. 2001 pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson. "Use of the LigaSure Vessel Sealing System in Bloodless Hemorrhoidectomy" That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales Product Literature.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.

(56) References Cited

OTHER PUBLICATIONS

Michael Choti, "Abdominoperineal Resection with the LigaSure Vessel Sealing System and LigaSure Atlas 20 cm Open Instrument"; Innovations That Work, Jun. 2003. (4 pages).
Chung et al., "Clinical Experience of Sutureless Closed Hemorrhoidectomy with LigaSure" Diseases of the Colon & Rectum vol. 46, No. 1 Jan. 2003, pp. 87-92.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003. (1 page).
Peterson et al. "Comparison of Healing Process Following Ligation with Sutures and Bipolar Vessel Sealing" Surgical Technology International (2001). (8 pages).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000. (1 page).
Johnson et al. "Evaluation of the LigaSure Vessel Sealing System in Hemorrhoidectormy" American College of Surgeons (ACS) Clinicla Congress Poster (2000). (1 page).
Muller et al., "Extended Left Hemicolectomy Using the LigaSure Vessel Sealing System" Innovations That Work, Sep. 1999. (4 pages).
Carus et al., "Initial Experience With the LigaSure Vessel Sealing System in Abdominal Surgery" Innovations That Work, Jun. 2002. (4 pages).
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002. (4 pages).
Koyle et al., "Laparoscopic Palomo Varicocele Ligation in Children and Adolescents" Pediatric Endosurgery & Innovative Techniques, vol. 6, No. 1, 2002, pp. 15-19.
W. Scott Helton, "LigaSure Vessel Sealing System: Revolutionary Hemostasis Product for General Surgery"; Sales/Product Literature 1999. (1 page).
LigaSure Vessel Sealing System, the Seal of Confidence in General, Gynecologic, Urologic, and Laparaoscopic Surgery; Sales/Product Literature; Apr. 2002. (8 pages).
Joseph Ortenberg "LigaSure System Used in Laparoscopic 1st and 2nd Stage Orchiopexy" Innovations That Work, Nov. 2002. (4 pages).
Olsson et al. "Radical Cystectomy in Females" Current Surgical Techniques in Urology, vol. 14, Issue 3, 2001. (8 pages).
Levy et al. "Randomized Trial of Suture Versus Electrosurgical Bipolar Vessel Sealing in Vaginal hysterectomy" Obstetrics & Gynecology, vol. 102, No. 1, Jul. 2003, pp. 147-151.
"Reducing Needlestick Injuries in the Operating Room" Sales/Product Literature 2001. (1 page).
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001. (1 page).
Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004. (1 page).
Rothenberg et al. "Use of the LigaSure Vessel Sealing System in Minimally Invasive Surgery in Children" Int'l Pediatric Endosurgery Group (IPEG) 2000. (1 page).
Craig Johnson, "Use of the LigaSure Vessel Sealing System in Bloodless Hemorrhoidectomy" Innovations That Work, Mar. 2000. (4 pages).
Levy et al. "Use of a New Energy-based Vessel Ligation Device During Vaginal Hysterectomy" Int'l Federation of Gynecology and Obstetrics (FIGO) World Congress 1999. (1 page).
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000. (1 page).
Jarrett et al., "Use of the LigaSure Vessel Sealing System for Peri-Hilar Vessels in Laparoscopic Nephrectomy" Sales/Product Literature 2000. (1 page).
McLellan et al. "Vessel Sealing for Hemostasis During Pelvic Surgery" Int'l Federation of Gynecology and Obstetrics FIGO World Congress 2000, Washington, D.C.. (1 page).
McLellan et al. "Vessel Sealing for Hemostasis During Gynecologic Surgery" Sales/Product Literature 1999. (1 page).
Heniford et al. "Initial Research and Clinical Results with an Electrothermal Bipolar Vessel Sealer" Oct. 1999. (1 page).
Vallfors et al., Automatically Controlled Bipolar Electrocoagulation—"COA-COMP", Neurosurg. Rev. (1984), pp. 187-190.
Examination Report No. 1 issued in corresponding Australian Application No. 2018201752 dated Aug. 8, 2018, 10 pages.
European Examination Report dated Jan. 3, 2020 issued in corresponding EP Appln. 18171773.7.

\* cited by examiner

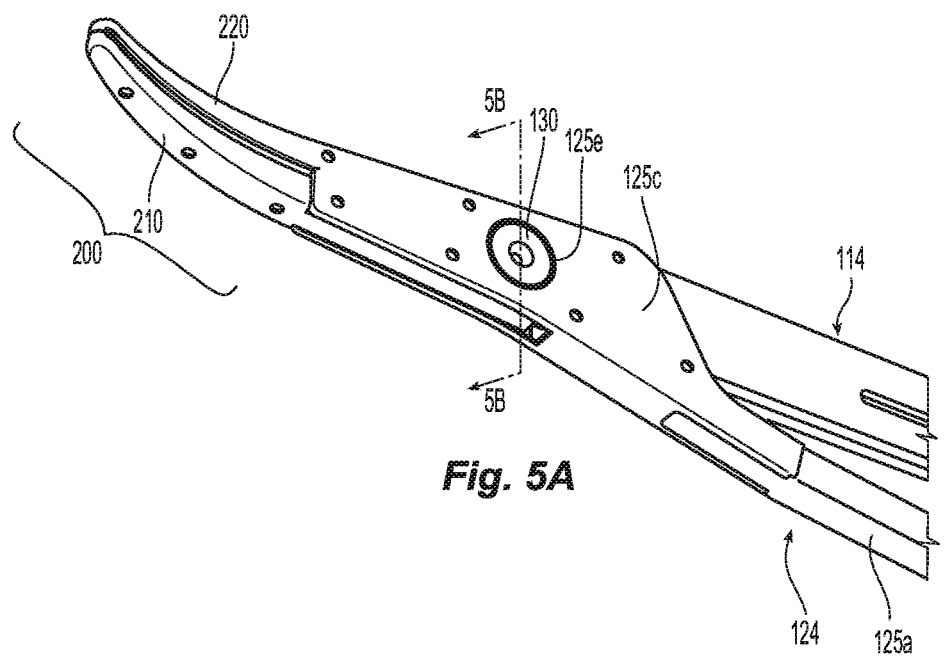
*Fig. 5A*
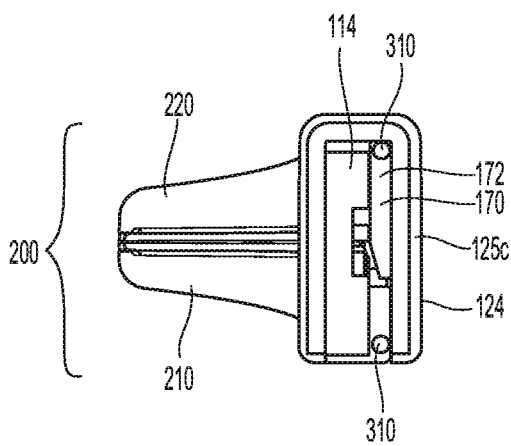
*Fig. 5B*
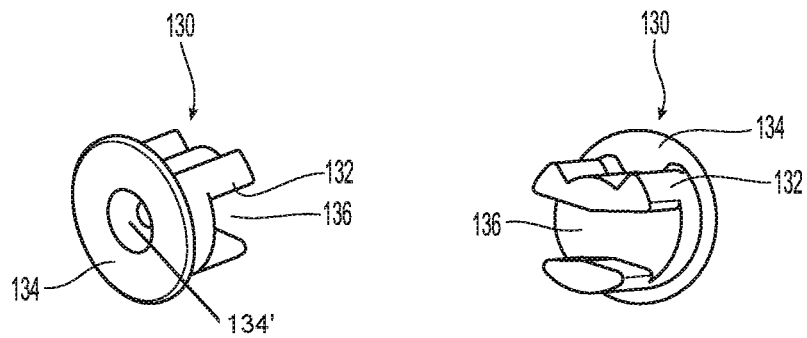
*Fig. 5C*          *Fig. 5D*

ELECTROSURGICAL FORCEPS FOR GRASPING, TREATING, AND/OR DIVIDING TISSUE

BACKGROUND

The present disclosure relates to electrosurgical instruments and, more particularly, to electrosurgical forceps for grasping, treating, and/or dividing tissue.

TECHNICAL FIELD

A surgical forceps is a plier-like instrument which relies on mechanical action between its jaws to grasp tissue. Electrosurgical forceps utilize both mechanical clamping action and electrical energy to treat tissue, e.g., coagulate, cauterize, and/or seal tissue.

Typically, once tissue is treated, the surgeon has to accurately sever the treated tissue. Accordingly, many electrosurgical forceps have been designed which incorporate a knife configured to effectively sever tissue after treating the tissue.

SUMMARY

As used herein, the term "distal" refers to the portion that is being described which is further from a surgeon, while the term "proximal" refers to the portion that is being described which is closer to a surgeon. Further, to the extent consistent, any of the aspects described herein may be used in conjunction with any or all of the other aspects described herein.

An electrosurgical forceps provided in accordance with aspects of the present disclosure includes first and second shaft members, a pivot member, a knife, a knife deployment mechanism, and a knife lockout. Each shaft member includes an inner frame, a jaw member secured to and extending distally from the inner frame, and an outer housing surrounding a portion of the inner frame. The pivot member pivotably couples the inner frames of the first and second shaft members to one another such that pivoting of the first and second shaft members relative to one another between spaced-apart and approximated positions pivots the jaw members relative to one another between open and closed positions. The knife is selectively translatable through the first shaft member from a retracted position to an extended position wherein the knife extends at least partially between the jaw members. The knife deployment mechanism is operably coupled to the first shaft member and includes at least one trigger and at least one linkage coupling the at least one trigger with the knife such that pivoting of the at least one trigger relative to the first shaft member translates the knife between the retracted and extended positions. The knife lockout includes a cantilever arm biased towards a locked position inhibiting distal translation of the knife. The cantilever arm is movable from the locked position to an unlocked position upon approximation of the jaw members to permit distal translation of the knife.

In an aspect of the present disclosure, the knife lockout further includes a body and a finger. The body forms a portion of the outer housing of the first shaft member. The cantilever arm extends from the body within the outer housing of the first shaft member. The finger extends from the cantilever arm externally of the outer housing of the first shaft member towards the second shaft member. In the approximated position of the first and second shaft members, the outer housing of the second shaft member is configured to contact the finger and urge the cantilever arm to the unlocked position permitting distal translation of the knife. The cantilever arm, the body, and the finger of the knife lockout may be a single, monolithic component.

In another aspect of the present disclosure, a pivot pin pivotably couples the at least one linkage of the knife deployment mechanism and the knife. In such aspects, in the locked position of the cantilever arm, the pivot pin is captured within a nook defined between the cantilever arm and the finger to inhibit distal translation of the knife.

In another aspect of the present disclosure, the inner frame of the first shaft member includes a body plate, a reinforcing plate secured to the body plate, and a channel defined between the body plate and a reinforcing plate. In such aspects, the knife is slidably disposed within the channel.

In yet another aspect of the present disclosure, the at least one linkage of the knife deployment mechanism includes a first linkage and a second linkage. The first linkage includes at least one boss at a first end portion thereof that engages the at least one trigger with the first linkage. The first linkage is pivotably coupled to a first end portion of the second linkage at a second end portion of the first linkage. The second linkage is pivotably coupled to the knife at a second end portion of the second linkage.

In still another aspect of the present disclosure, the inner frame of the first shaft member defines an aperture through which one of the at least one bosses of the first linkage extends to pivotably couple the first linkage to the first shaft member.

In still yet another aspect of the present disclosure, the first linkage is disposed on one side of the inner frame of the first shaft member and the second linkage is disposed on an opposite side of the inner frame of the first shaft member. Further, the cantilever arm of the knife lockout may be disposed on the same side of the inner frame of the first shaft member as the first linkage.

In another aspect of the present disclosure, the first and second shaft members each further include a handle engaged with a support plate. The support plates are secured within the outer housings of the respective shaft members.

In still another aspect of the present disclosure, a biasing member is operably coupled between the support plate of the first shaft member and the knife deployment mechanism to bias the knife towards the retracted position.

In yet another aspect of the present disclosure, the electrosurgical forceps further includes first and second lead wires, an electrosurgical cable, and a switch assembly. The first and second lead wires extend through the second shaft member and electrically couple to the first and second jaw members, respectively. The electrosurgical cable is coupled to the second shaft member and adapted to connect to a source of electrosurgical energy. The switch assembly is disposed on the second shaft member, includes an activation button, and electrically couples the first and second lead wires, the electrosurgical cable, and the activation button with one another such that actuation of the activation button supplies electrosurgical energy to the first and second jaw members.

In still yet another aspect of the present disclosure, in the approximated position of the first and second shaft members, the first shaft member is configured to actuate the activation button.

In another aspect of the present disclosure, the switch assembly further includes a Printed Circuit Board (PCB) having the activation button mounted on a central portion thereof, the electrosurgical cable electrically coupled to a first end portion thereof, and the first and second lead wires electrically coupled to a second end portion thereof. The switch assembly further includes circuit traces defined on the PCB and electrically coupling the electrosurgical cable, the activation button, and the first and second lead wires with one another.

In still another aspect of the present disclosure, the switch assembly further includes at least one quick-connect receptacle disposed on the PCB at the second end portion thereof. The at least one quick-connect receptacle is configured to facilitate electrical coupling of the first and second lead wires with the PCB.

In another aspect of the present disclosure, the jaw member of the first shaft member includes a jaw support engaged with the inner frame of the first shaft member, and an insulative housing surrounding a portion of the jaw support and extending proximally about a portion of the inner frame of the first shaft member, and an electrically-conductive tissue-contacting plate disposed on the jaw support and partially surrounded by the insulative housing.

In yet another aspect of the present disclosure, the jaw support is secured to the inner frame of the first shaft member and/or the insulative housing is overmolded about the jaw support and the portion of the inner frame of the first shaft member.

In still another aspect of the present disclosure, a proximally-extending portion of the jaw support overlaps the inner frame of the first shaft member and defines a roof configured to receive a distal cutting portion of the knife in the retracted position of the knife.

In another aspect of the present disclosure, the knife extends through a slot defined in the pivot member. Further, the knife may include a stop shoulder inhibited from passing through the slot in the pivot member such that the stop shoulder abuts the pivot member in a distal-most position of the knife, thereby defining the distal-most position of the knife.

In still yet another aspect of the present disclosure, in the approximated position of the first and second shaft members, the at least one trigger is fully disposed within a height dimension of the first and second shaft members such that the at least one trigger does not extend beyond the height dimension of the first and second shaft members.

BRIEF DESCRIPTION OF THE DRAWINGS

Various aspects and features of the present disclosure are described hereinbelow with reference to the drawings wherein like numerals designate identical or corresponding elements in each of the several views:

FIG. 5A is a perspective view of a distal portion of the forceps of FIG. 1 illustrating the first and second jaw members pivotably coupled to form the end effector assembly;

FIG. 5B is a transverse, cross-sectional view taken along section line "5B-5B" in FIG. 5A;

FIG. 5C is a first perspective view of a pivot member of the end effector assembly of the forceps of FIG. 1

FIG. 5D is a second perspective view of the pivot member of the end effector assembly of the forceps of FIG. 1;

DETAILED DESCRIPTION

Figure 1:
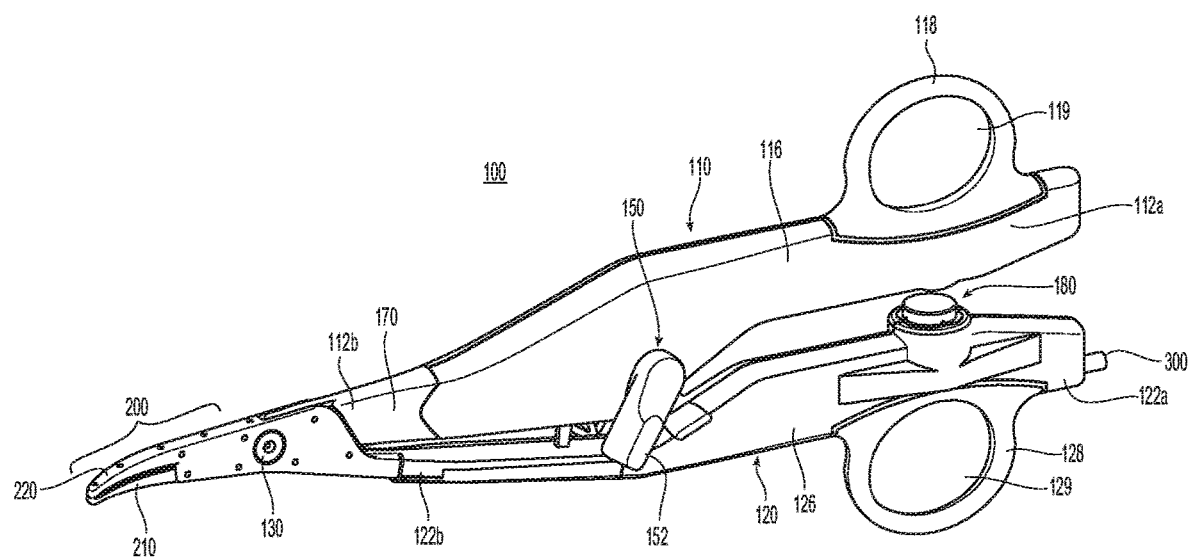
FIG. 1 is a side, perspective view of an electrosurgical forceps provided in accordance with aspects of the present disclosure.
Figure 2A:
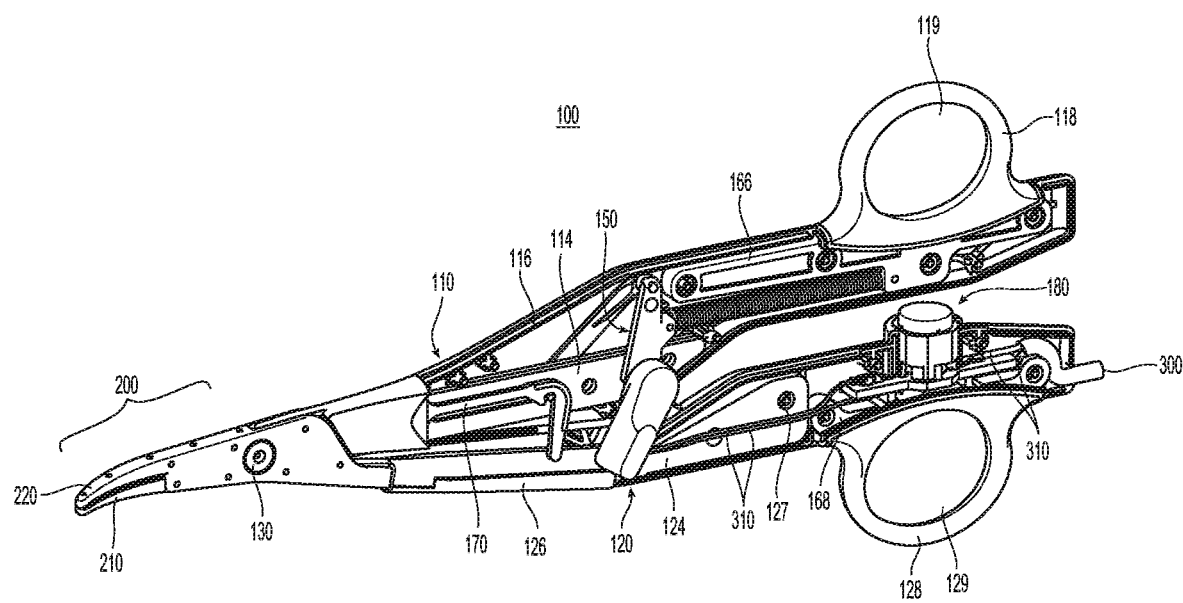
FIG. 2A is a perspective view from one side of the forceps of FIG. 1 with portions of outer housings of first and second shaft members removed to illustrate the internal components therein.
Figure 2B:
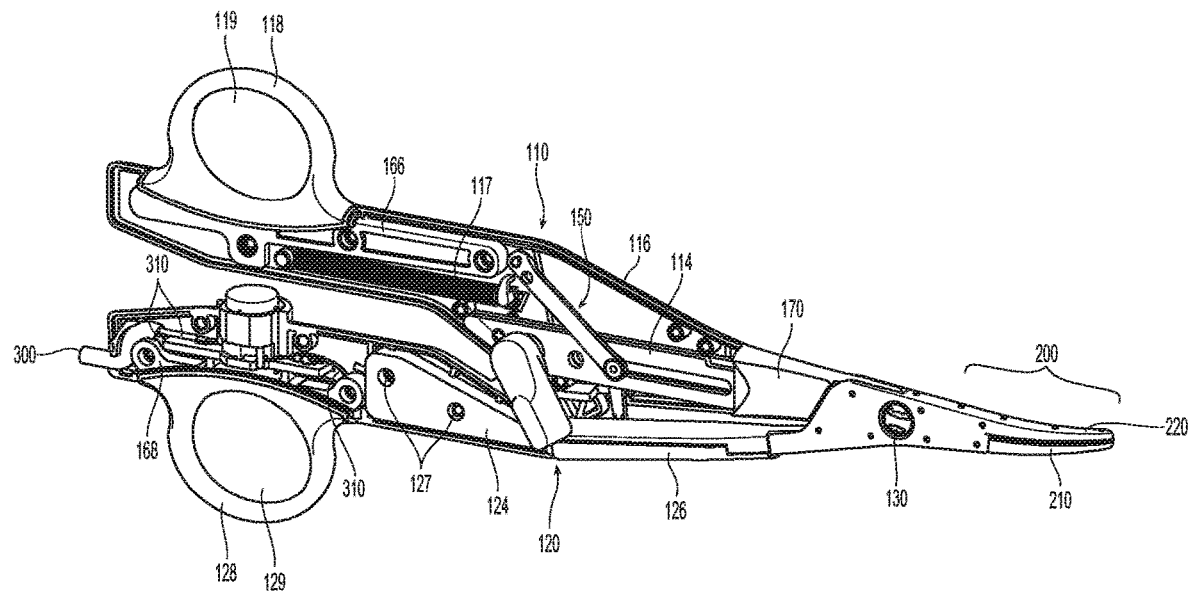
FIG. 2B is a perspective view from the other side of the forceps of FIG. 1 with other portions of the outer housings of the shaft members removed to illustrate the internal components therein.
Figure 9:
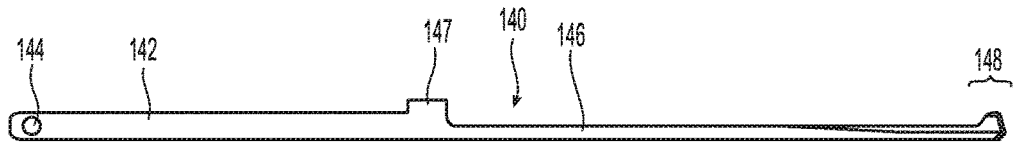
FIG. 9 is a side view of a knife of the forceps of FIG. 1.
Figure 10:
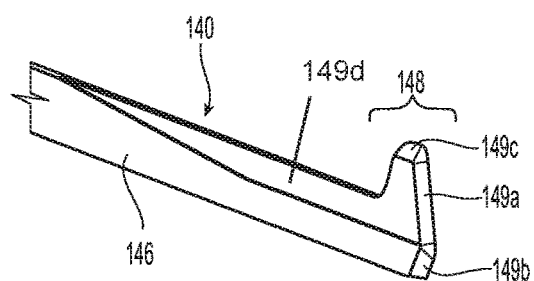
FIG. 10 is a perspective view of a distal portion of the knife of FIG. 9.

Referring generally to FIGS. 1-2B, a forceps 100 provided in accordance with the present disclosure includes first and second shaft members 110, 120 each having a proximal end portion 112a, 122a and a distal end portion 112b, 122b. An end effector assembly 200 of forceps 100 includes first and second jaw members 210, 220 extending from distal end portions 112b, 122b of shaft members 110, 120, respectively. Forceps 100 further includes a pivot member 130 pivotably coupling first and second shaft members 110, 120 with one another, a knife 140 (FIGS. 9-10), a knife deployment mechanism 150 for selectively deploying knife 140 (FIGS. 9-10) relative to end effector assembly 200, a knife lockout 170 for inhibiting deployment of knife 140 (FIGS. 9-10)

prior to sufficient closure of jaw members 210, 220, and a switch assembly 180 for enabling the selective supply of electrosurgical energy to end effector assembly 100. An electrosurgical cable 300 electrically couples forceps 100 to a source of energy (not shown), e.g., an electrosurgical generator, to enable the supply of electrosurgical energy to jaw members 210, 220 of end effector assembly 200 upon activation of switch assembly 180.

Continuing with reference to FIGS. 1-2B, each shaft member 110, 120 includes an inner frame 114, 124, an outer housing 116, 126 surrounding at least a portion of the respective inner frame 114, 124, and a handle 118, 128 engaged with the respective outer housing 116, 126 towards proximal end portions 112a, 122a of shaft members 110, 120, respectively. Inner frames 114, 124 are described in greater detail below. Outer housings 116, 126 enclose and/or operably support the internal components disposed within shaft members 110, 120. More specifically, as detailed below, outer housing 116 of shaft member 110 encloses and supports at least a portion of inner frame 114, knife deployment mechanism 150, and lockout 170, while outer housing 126 of shaft member 120 receives electrosurgical cable 300 and encloses and supports at least a portion of inner frame 124, switch assembly 180, and the lead wires 310 of electrosurgical cable 300. Handles 118, 128 are engaged with outer housings 116, 126 towards proximal end portions 112a, 112b of shaft members 110, 120 and extend outwardly from shaft members 110, 120. Handles 118, 128 define finger holes 119, 129 configured to facilitate grasping and manipulating shaft members 110, 120.

Figure 3A:
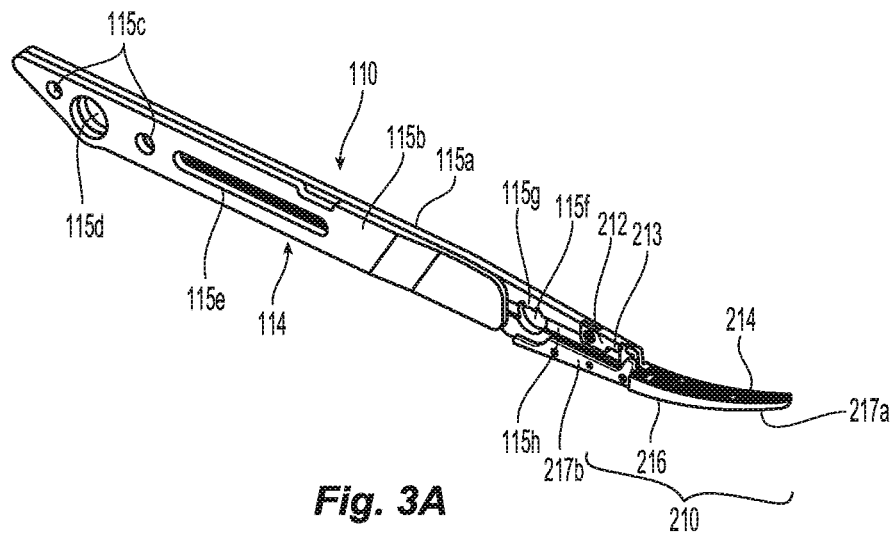
FIG. 3A is a perspective view of an inner frame and a jaw member of the first shaft member of the forceps of FIG. 1.

Referring to FIG. 3A, inner frame 114 of shaft member 110 includes a body plate 115a and a reinforcing plate 115b attached to body plate 115a, e.g., via welding, to provide increased lateral stiffness and structural support thereto. In embodiments, reinforcing plate 115b may be welded to body plate 115a in at least two places, e.g., towards the proximal and distal end portions thereof. The increased lateral stiffness provided by reinforcing plate 115b helps ensure alignment of depressible button 183b (FIG. 16A) of switch assembly 180 with outer housing 116 of shaft member 110 (Fig. such that depressible button 183b is depressed and switch assembly 180 activated upon sufficient approximation of shaft members 110, 120 (see also FIG. 15).

Inner frame 114 defines one or more location apertures 115c, a trigger aperture 115d, and a longitudinal slot 115e that each extend through both body plate 115a and reinforcing plate 115b. The one or more location apertures 115c are configured to receive corresponding posts 117 of outer housing 116 to locate and maintain inner frame 114 in position within outer housing 116. Body plate 115a extends distally beyond reinforcing plate 115b to enable attachment of jaw support 212 of jaw member 210 thereto, e.g., via staking or other suitable engagement. The portion of body plate 115a that extends distally beyond reinforcing plate 115b further defines a pivot aperture 115f extending transversely therethrough. A stop protrusion 115g extends from inner frame 114 into pivot aperture 115f, as detailed below. Body plate 115a of inner frame 114 further defines a longitudinal channel 115h oriented towards reinforcing plate 115b such that reinforcing plate 115b encloses a portion of longitudinal channel 115h.

Figure 3B:
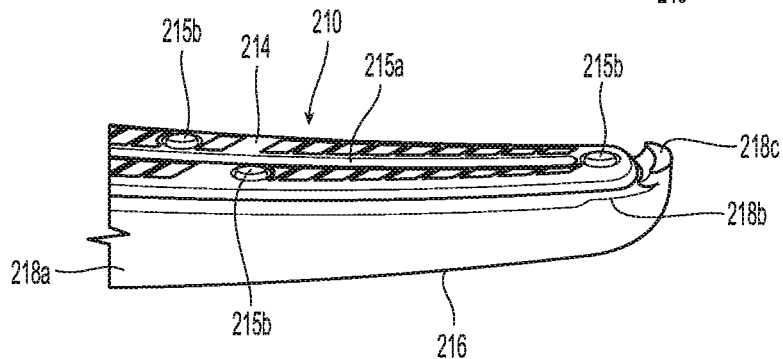
FIG. 3B is an enlarged, side, perspective view of a distal portion of the jaw member of FIG. 3A.

With additional reference to FIG. 3B, as noted above, jaw support 212 of jaw member 210 is staked or otherwise engaged, e.g., welded, press-fit, mechanically locked, etc., to the portion of body plate 115a that extends distally beyond reinforcing plate 115b. Jaw member 210 further includes an electrically-conductive, tissue-contacting plate 214 and an insulative housing 216. Tissue-contacting plate 214 defines a longitudinally-extending knife channel 215a extending at least partially therethrough and may include one or more stop members 215b disposed thereon and electrically isolated therefrom. Insulative housing 216 of jaw member 210 is overmolded or otherwise secured about a portion of jaw support 212, tissue-contacting plate 214, and body plate 115a of inner frame 114 of shaft member 110. Insulative housing 216 includes a distal portion 217a and a proximal extension portion 217b. Proximal extension portion 217b of insulative housing 216 is configured to extend proximally along body plate 115a of inner frame 114 to (or proximally beyond) pivot aperture 115f thereof. The electrical lead 310 (FIGS. 2A and 3B) configured to electrically couple to tissue-contacting plate 214 is captured between body plate 115a and proximal extension portion 217b of insulative housing 216 to protect and facilitate routing of the electrical lead 310 (FIGS. 2A and 3B) from shaft member 120, around pivot aperture 115f, and distally therefrom to electrically couple to tissue-contacting plate 214.

Distal portion 217a of insulative housing 216 of jaw member 210 extends about the periphery of tissue-contacting plate 214 and defines a main section 218a, a raised section 218b, and a beak section 218c. Main section 218a of distal portion 217a of insulative housing 216 extends on either side of tissue-contacting plate 214 and is offset relative thereto such that tissue-contacting plate 214 is raised relative to main section 218a. Raised section 218b of distal portion 217a of insulative housing 216 extends distally from main section 218a on either side of tissue-contacting plate 214 and is still recessed relative to tissue-contacting plate 214 but is closer to being co-planar with tissue-contacting plate 214 as compared to main section 218a. Beak section 218c of distal portion 217a of insulative housing 216 is disposed distally of tissue-contacting plate 214 and extends to or beyond tissue-contacting plate 214. Beak section 218c inhibits tissue from entering the area between jaw members 210, 220 of end effector assembly 200 when end effector assembly 200 is disposed in the closed position and utilized for blunt dissection (see FIG. 5A).

Figure 3C:
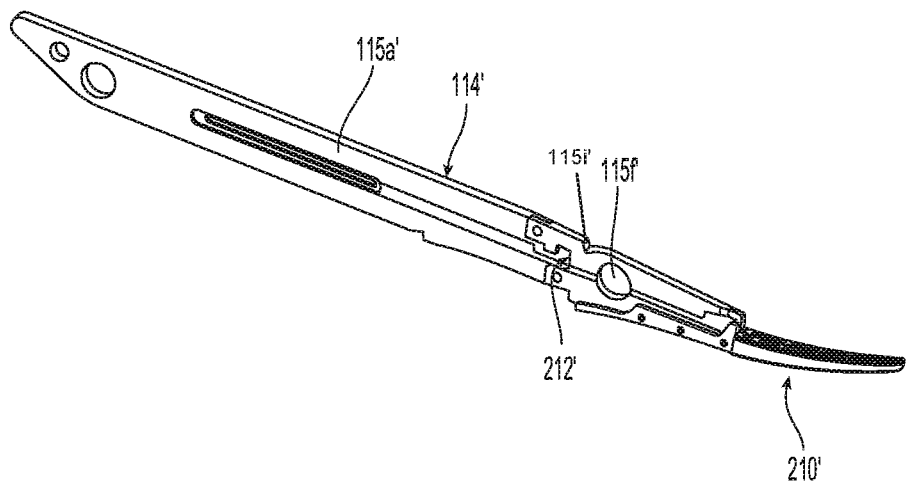
FIG. 3C is perspective view of another body plate of the inner frame and jaw member configured for use with the forceps of FIG. 1.

Referring to FIG. 3C, another embodiment is provided wherein body plate 115a' of inner frame 114' does not define the pivot aperture therethrough but, rather, terminates proximally of the pivot location. In this embodiment, jaw support 212' of jaw member 210' defines pivot aperture 115f' and extends from the distal body portion of jaw member 210' proximally beyond the pivot location to enable jaw support 212' to be staked or otherwise engaged to body plate 115a' of inner frame 114' proximally of the pivot location. Pivot aperture 115f' defined within jaw support 212' receives pivot member 130 similarly as detailed above with regard to pivot aperture 115f (se FIGS. 3A and 5C). In this embodiment, jaw support 212' may include, in the areas where jaw support 212' replaces body plate 115a (FIG. 3A), any of the features of body plate 115a of inner frame 114 (see FIG. 3A) and may likewise include any of the features of jaw support 212 (FIG. 3A).

Continuing with reference to FIG. 3C, in embodiments, the jaw support, e.g., jaw support 212', may further define a notch 115i' configured to receive an edge 125g (FIG. 17B) of distal clevis portion 125c of inner frame 124 of shaft member 120 (FIG. 4A) therein to define the spaced-apart position of shaft members 110, 120 (see FIGS. 2A-2B). That is, receipt of edge 125g (FIG. 17B) within notch 115i' inhibits further movement of shaft members 110, 120 apart from one another, thus defining the furthest spaced-apart portion of shaft member 110, 120 (see FIGS. 2A-2B).

Figure 4A:
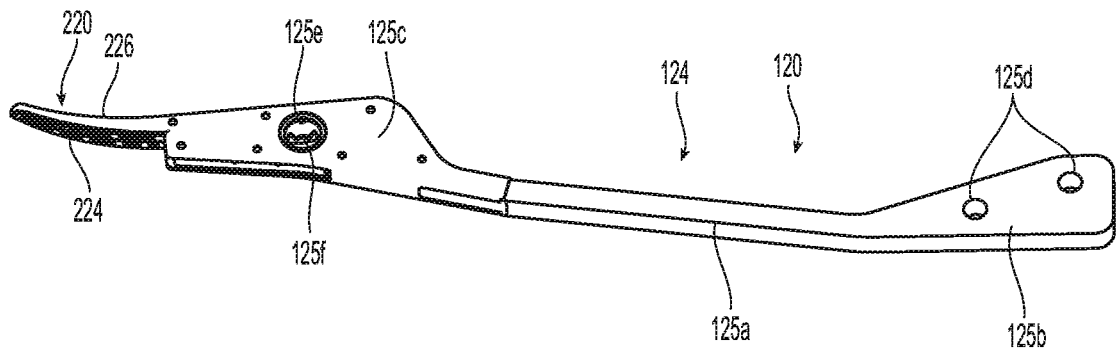
FIG. 4A is a perspective view of an inner frame and a jaw member of the second shaft member of the forceps of FIG. 1.

Turning to FIG. 4A, inner frame 124 of shaft member 120 includes an elongated body portion 125a, an enlarged proximal portion 125b, and a distal clevis portion 125c. Enlarged proximal portion 125b of inner frame 124 provides additional structural support to shaft member 120 and defines one or more location apertures 125d that, similarly as with location apertures 115c of inner frame 114 of shaft member 110 (FIG. 3A), are configured to receive corresponding posts 127 of outer housing 126 to locate and maintain inner frame 124 in position within outer housing 126. Elongated body portion 125a of inner frame 124 extends through outer housing 126 of shaft member 120, while distal clevis portion 125c of shaft member 120 extends distally from outer housing 126. Distal clevis portion 125c may be welded to, monolithically formed with, or otherwise engaged to elongated body portion 125a of inner frame 124. Distal clevis portion 125c of inner frame 124 is detailed below.

Figure 4B:
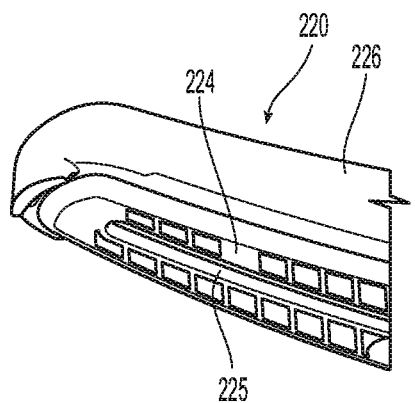
FIG. 4B is an enlarged, perspective view of a distal portion of the jaw member of FIG. 4A.

Elongated body portion 125a defines a flexibility, e.g., is flexible an amount according to a spring constant thereof, thus enabling flexure of elongated body portion 125a in response to application of a jaw force at jaw member 220. This configuration enables the application of a jaw force within a particular range, e.g., between about 3 kg/cm$^2$ and about 16 kg/cm$^2$, when shaft members 110, 120 are disposed in the approximated position corresponding to the closed position of jaw members 210, 220. Referring also to FIGS. 3A, 3B, and 4B, in embodiments, in addition to the flexion of elongated body portion 125a providing a jaw force within a particular range, flexion of the jaw members 210, 220 may also contribute to providing a jaw force within a particular range. More specifically, due to the relatively fine configuration of the jaw members 210, 220 and the fact that the jaw members 210, 220 taper in height and width from the proximal ends to the distal ends thereof, the jaw members 210, 220 themselves provide flexibility that, in conjunction with the flexibility of elongated body portion 125a, provide a jaw force within a particular range to facilitate tissue treatment.

Referring to FIGS. 4A and 4B, jaw member 220 of end effector assembly 200 is supported on a distal extension (not shown) of distal clevis portion 125c of inner frame 124 of shaft member 120. The distal extension (not shown) of distal clevis portion 125c of inner frame 124 serves as the jaw frame of jaw member 220. Jaw member 220 further includes an electrically-conductive, tissue-contacting plate 224 and an insulative housing 226. Tissue-contacting plate 224 defines a longitudinally-extending knife channel 225 extending at least partially therethrough and may include one or more stop members, similarly as with jaw member 210 (FIG. 3B). Insulative housing 226 of jaw member 220 is similar to that of jaw member 210 (FIG. 3B) and, thus, the features thereof will not be repeated here.

As illustrated in FIGS. 1 and 3A-4B, jaw members 210, 220 taper in height and width from the proximal ends to the distal ends thereof, thus facilitating blunt dissection and inhibiting jaw splay. Jaw members 210, 220 also define curved configurations that facilitate visualization of the surgical site and provide increased surface area for grasping tissue.

With reference to FIGS. 5A-5B, distal clevis portion 125c of inner frame 124 of shaft member 120 and body plate 115a of inner frame 114 of shaft member 110 are pivotably coupled to one another via pivot member 130 such that shaft members 110, 120 are movable relative to one another between spaced-apart and approximated positions to thereby pivot jaw members 210, 220 relative to one another between open and closed positions. More specifically, distal clevis portion 125c and body plate 115a define a lock-box configuration wherein distal clevis portion 125c includes a bifurcated, U-shaped configuration having an elongated slot defined therein, and wherein body plate 115a is configured for nested receipt within the elongated slot of the bifurcated, U-shaped distal clevis portion 125c. Referring in particular to FIG. 5B, sufficient clearance is provided between distal clevis portion 125c and body plate 115a when body plate 115a is nested within distal clevis portion 125c such that lead wires 310 are permitted to extend therethrough, ultimately to electrically couple tissue-contacting plates 214, 224 (FIGS. 3B and 4B, respectively) to switch assembly 180 (FIGS. 1-2B) and the source of energy (not shown). Further, body 172 of knife lockout 170 is configured for positioning adjacent body plate 115a within distal clevis portion 125c to minimize lateral play between body plate 115a and distal clevis portion 125c and to act as a wire guide to maintain the lead wires 310 for jaw member 210 distally spaced-apart from pivot member 130. With respect to acting as a wire guide, body 172 of knife lockout 170 inhibits the lead wire 310 for jaw member 210 from interfering with and being damaged during the pivoting of shaft members 110, 120 about pivot member 130, and inhibits the lead wire 310 for jaw member 210 from interfering with and being damaged by translation of knife 140.

Referring also to FIGS. 5C-5D, pivot member 130 includes a body 132 and a cap 134. Body 132 of pivot member 130 is configured to extend through an aperture 125e defined through one of the side walls of distal clevis portion 125c of inner frame 124 of shaft member 120, pivot aperture 115f of body plate 115a of inner frame 114 of shaft member 110, and into a keyed aperture (or apertures) 125f defined through the other side wall of distal clevis portion 125c in fixed rotational orientation relative thereto. Body portion 132 of pivot member 130 is configured to be welded to the portion of the side wall of distal clevis portion 125c that surrounds keyed aperture(s) 125f. More specifically, the keying of body portion 132 within keyed aperture(s) 125f maintains proper orientation of pivot member 130 during welding. Body 132 is further configured to abut stop protrusion 115g (FIG. 3A) upon pivoting of shaft members 110, 120 away from one another to define a furthest-spaced apart position of shaft members 110, 120 and, similarly, a most-open position of jaw members 210, 220. A slot 136 defined through body 132 of pivot member 130 is configured to permit translation of knife 140 (FIGS. 9-10) therethrough, as detailed below.

Cap 134 of pivot member 130 defines a location recess 134' therein, as illustrated in FIG. 5C, for example, although other configurations are also contemplated. Location recess 134' is described below with respect to the assembly of forceps 100.

Turning to FIGS. 1 and 6-8, knife deployment mechanism 150 is coupled to shaft member 110 and generally includes a pair of opposed triggers 152 extending from either side of shaft member 110, first and second linkages 154, 156, and a biasing spring 158. Knife deployment mechanism 150 is disposed within outer housing 116 of shaft member 110 with the exception of opposed triggers 152 which extend from either side of outer housing 116. First linkage 154 is configured for positioning on one side of inner frame 114 of shaft member 110 and includes a pair of integral (or otherwise engaged) pivot bosses 161 extending from either side thereof at a first end portion of first linkage 154. One of the pivot bosses 161 extends through trigger aperture 115d of inner frame 114 (see FIG. 3A). Each pivot boss 161 extends through an aperture defined through outer housing 116 of shaft member 110 to enable engagement of opposed triggers 152 therewith on either side of shaft member 110, e.g., via press-fitting, adhesion, or other suitable engagement.

Figure 6:
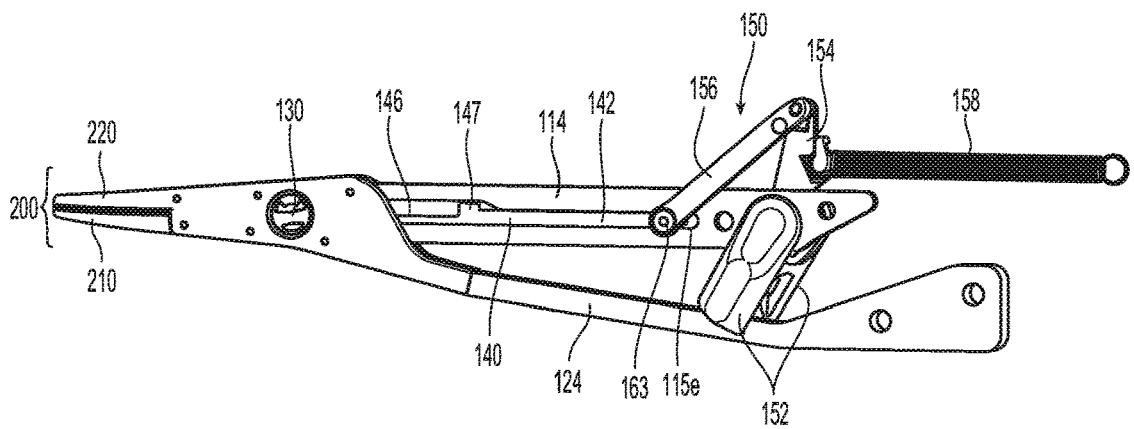
FIG. 6 is a side, perspective view of the forceps of FIG. 1 with portions removed to illustrate a knife deployment mechanism of the forceps.
Figure 7:
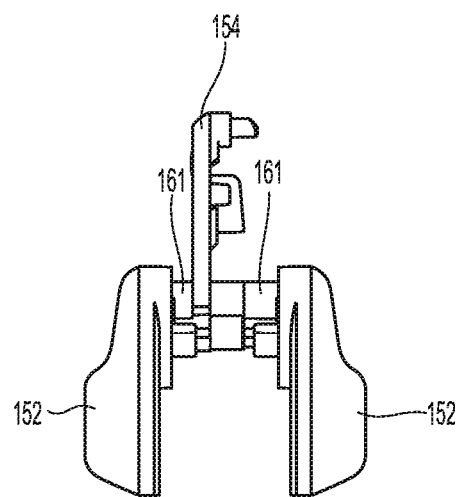
FIG. 7 is a rear view of a pair of triggers and a first linkage of the knife deployment mechanism of FIG. 6.
Figure 8:
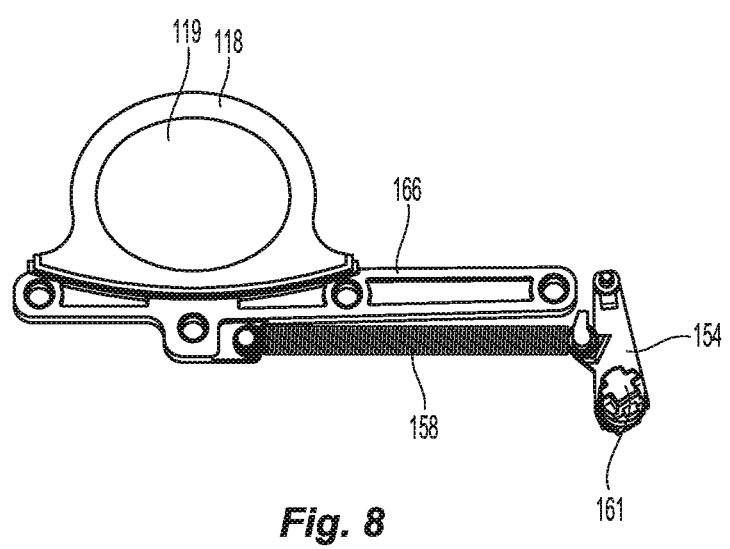
FIG. 8 is a side view of a handle of the first shaft member of the forceps of FIG. 1 shown operably coupled to a first linkage of the knife deployment mechanism of FIG. 6.

Referring to FIGS. 6-8, a proximal end portion of second linkage 156 is pivotably coupled to first linkage 154 at a second end portion of first linkage 154. However, greater or fewer linkages 154, 156 are also contemplated. A distal end portion of second linkage 156 is pivotably coupled to knife 140 (see also FIGS. 9-10) via a pivot pin 163. Pivot pin 163 may be integrally formed with second linkage 156, e.g., as a post extending therefrom, or may be a separate component from second linkage 156. Pivot pin 163 extends transversely through longitudinal slot 115e of inner frame 114 of shaft member 114 such that pivot pin 163 is constrained to longitudinal movement within longitudinal slot 115e. Second linkage 156 is disposed on one side of inner frame 114, which may be the same side as first linkage 154 or the opposite side (as shown). In either configuration, pivot pin 163 extends from second linkage 156 and through longitudinal slot 115e such that a portion of pivot pin 163 protrudes laterally from the opposite side of inner frame 114.

Biasing spring 158 may be configured as an extension spring or other suitable biasing spring 158 and is engaged at a distal end portion thereof to first linkage 154 and at a proximal end portion thereof to a support plate 166. Support plate 166 includes handle 118 of shaft member 110 integrally formed therewith or otherwise engaged thereto, and may be secured within outer housing 116 in any suitable fashion, e.g., via protrusion-aperture engagement. Support plate 166 provides increased structural support to shaft member 110 to inhibit splaying of shaft members 110, 120 during use. Shaft member 120 similarly includes a support plate 168 integrally formed with or otherwise engaging handle 128 of shaft member 120 and secured to outer housing 126, although support plate 168 need not extend distally as with support plate 166 (see FIGS. 2A and 2B).

Biasing spring 158 biases first linkage 154 towards a first orientation, corresponding to the un-actuated position of triggers 152 and the proximal-most position of second linkage 156, thereby biasing knife 140 towards the retracted position. Upon rotation of either of triggers 152 relative to shaft member 110, first linkage 154 is rotated against the bias of biasing spring 158 to thereby urge second linkage 156 distally such that pivot pin 163 is driven distally though longitudinal slot 115e to urge knife 140 from the retracted position towards an extended position, wherein knife 140 extends through slot 136 of pivot member 130 and channels 215a, 225 of jaw members 210, 220 (FIGS. 3B and 4B, respectively).

Referring to FIGS. 9 and 10, knife 140 includes a proximal body 142 defining an aperture 144 through which knife 140 is pivotably coupled to second linkage 156 of knife deployment mechanism 150 via pin 163 (see FIG. 6). Proximal body 142 is slidably disposed within channel 115h between body plate 115a and reinforcing plate 115b of inner frame 114 of shaft member 110 (see FIG. 3A). Knife 140 further includes a distal body 146 defining a lower profile as compared to proximal body 142 and extending distally from proximal body 142. Distal body 146 defines a distal cutting portion 148. Distal cutting portion 148 defines an enlarged height as compared to distal body 146 and may be etched to define an asymmetrically sharpened configuration wherein one side of distal cutting portion 148 extends further distally than the opposite side (due to the removal of material from the opposite side during the etching process). The enlarged height of distal cutting portion 148 helps ensure that distal cutting portion 148 extends fully through the gap defined between jaw members 210, 220 (FIG. 1) and is at least partially received in respective knife channels 215a, 225 thereof (see FIGS. 3B and 4B). In the retracted position of knife 140, the enlarged height of distal cutting portion 148 is configured for receipt within a roof 213 defined by a proximally-extending portion of jaw support 212 of jaw member 210 (see FIG. 3A). The etched distal cutting edge of distal cutting portion 148 defines three segments: a main cutting segment 149a, a lower cutting segment 149b extending from one end of main cutting segment 149a at an angle relative thereto, and an upper cutting segment 149c extending from the opposite end of main cutting segment 149a at an angle relative thereto.

Knife 140 further includes a partial etch 149d extending along a portion of distal body 146 and distal cutting portion 148 of knife 140. Partial etch 149d may extend along either or both sides of knife 140. Partial etch 149d is configured to inhibit wear of knife 140, to promote flexibility to facilitate translation of knife 140 through knife channels 215a, 225 of jaw members 210, 220 (see FIGS. 3A-4B), to facilitate smooth translation of knife 140 through knife channels 215a, 225 (see FIGS. 3A-4B) should partial etch 149d come in contact with the sidewalls defining channels 215a, 225 (see FIGS. 3A-4B), and to provide greater clearance between knife 140 and the sidewalls defining channels 215a, 225 (see FIGS. 3A-4B).

In use, distal body 146 of knife 140 is configured to reciprocate through slot 136 of pivot member 130 (FIG. 5D) to translate distal cutting edge 148 through knife channels 215a, 225 of jaw members 210, 220 in response to actuation of either of triggers 152 (see FIGS. 2A-4B). Knife 140 further includes a stop shoulder 147 defined at the transition between proximal body 142 and distal body 146. Stop shoulder 147 defines a height greater than a height of slot 136 of pivot member 130 (FIG. 5D) such that stop shoulder 147 is inhibited from passing therethrough. Accordingly, stop shoulder 147 defines the distal-most extent of travel of knife 140, e.g., wherein stop shoulder 147 abuts pivot member 130 (FIG. 5D). Alternatively, rather than abutting pivot member 130, stop shoulder 147 may abut a portion of distal clevis portion 125c defining keyed aperture(s) 125f for similar purposes.

With momentary reference to FIGS. 1 and 2A, knife deployment mechanism 150 is operably positioned on shaft member 110 and relative to shaft member 120 such that such that triggers 152 do not extend beyond the height dimension of forceps 100 in the vicinity of triggers 152, even in the furthest-approximated position of shaft members 110, 120. As a result of this configuration, forceps 100 benefits from a low-profile design that inhibits triggers 152 from catching on the surgeon, patient, or on nearby objections during use and/or as forceps 100 is inserted and withdrawn from the surgical site.

Figure 12A:
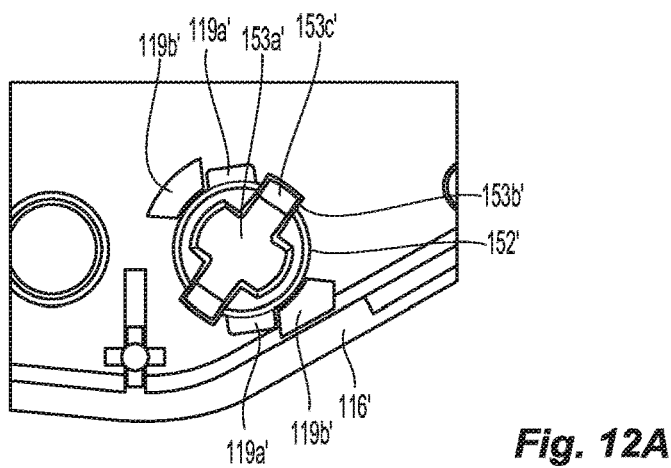
FIGS. 12A and 12B are enlarged, internal views illustrating rotation of the connector end of the trigger of FIG. 11A within the keyed aperture of the outer housing of the first shaft member of FIG. 11B.
Figure 12B:
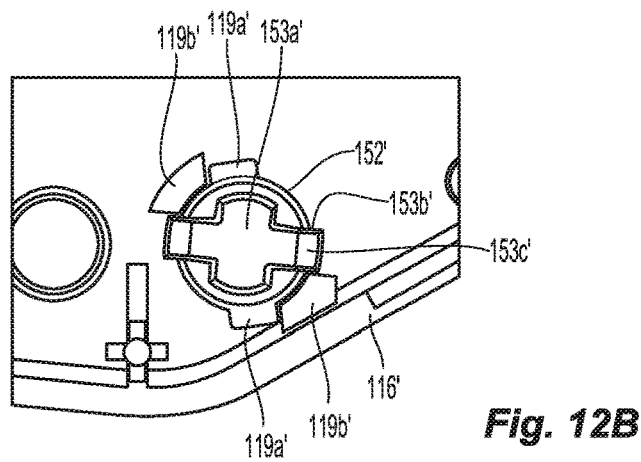
Figure 13:
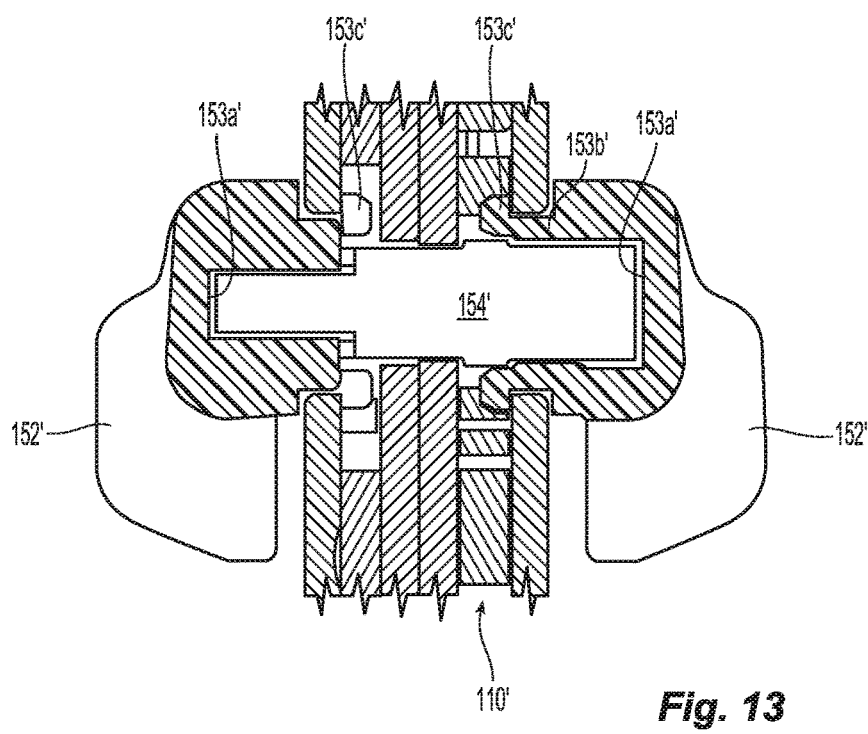
FIG. 13 is a transverse, cross-sectional view illustrating the pair of triggers of FIG. 11A engaged with the outer housing of the first shaft member of FIG. 11B and the knife deployment mechanism of FIG. 6.

Referring to FIGS. 11A-13, in some embodiments, each trigger 152' may be provided with a non-circular aperture 153a' configured to receive a correspondingly-shaped pivot boss (not shown) of first linkage 154' (FIG. 13). In such embodiments, each trigger 152' may further include a pair of opposed cantilever arms 153b' extending from opposite sides of non-circular aperture 153a'. As detailed below, cantilever arms 153b' include fingers 153c' configured to operably engage outer housing 116' to retain triggers 152' in engagement with first linkage 154' (FIG. 13) without the need for press-fitting.

Figure 11A:
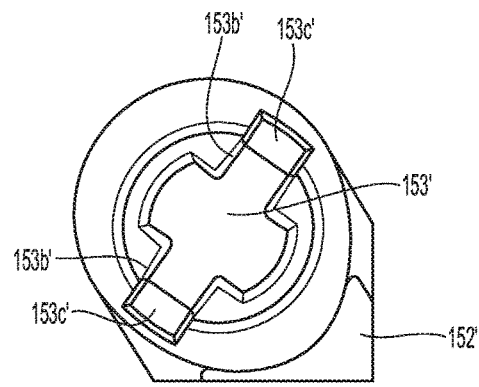
FIG. 11A is an enlarged, side view of a connector end of one of the pair of triggers configured for use with the knife deployment mechanism of FIG. 6.
Figure 11B:
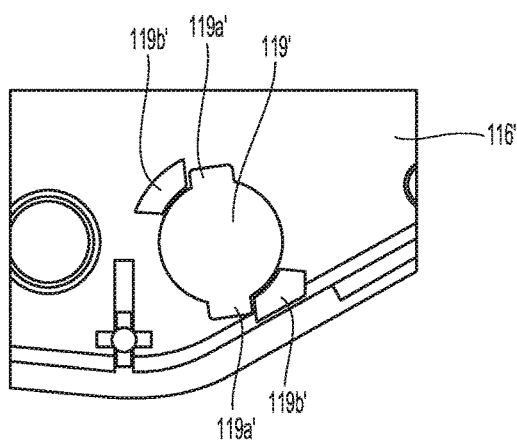
FIG. 11B is an enlarged, side view of a portion of the outer housing of the first shaft member of the forceps of FIG. 1 including a keyed aperture configured to receive the connector end of the trigger of FIG. 11A.

With reference to FIG. 11B, in order to operably engage triggers 152', outer housing 116' defines a pair of opposed apertures 118' (only one of which is shown) defining a pair of cut-outs 119a'. Outer housing 116' further includes a stop protrusion 119b' on an inner surface thereof adjacent each cut-out 119a'.

Referring to FIGS. 12A and 12B, in order to engage triggers 152' with outer housing 116', triggers 152' are oriented such that non-circular apertures 153a' are aligned relative to the correspondingly-shaped pivot bosses (not shown) and such that cantilever arms 153b' are aligned relative to cut-outs 119a'. Thereafter, triggers 152' are advanced such that the pivot bosses (not shown) are received within non-circular apertures 153a' and such that cantilever arms 153b' extend sufficiently through cut-outs 119a' and into outer housing 116' such that fingers 153c' are disposed internally of outer housing 116'. Once this position has been achieved, triggers 152' are rotated relative to outer housing 126 such that fingers 153c' are no longer aligned with cut-outs 129a' and, accordingly, such that triggers 152' are inhibited from backing out of apertures 128'. Thereafter, first linkage 154' is coupled to the other components of the knife deployment mechanism, e.g., similarly as detailed above. This engagement of first linkage 154' with the other components defines a range of motion of first linkage 154' and, more specifically, limits the range of motion thereof such that, in conjunction with stop protrusions 119b', first linkage 154' inhibits triggers 152' from rotating back to a position wherein cantilever arms 153b' are aligned relative to cut-outs 119a'. Thus, disengagement of triggers 152' from outer housing 116' and first linkage 154' are inhibited without requiring press-fit, adhesion, or other backout-preventing engagement between triggers 152' and first linkage 154'.

Figure 14:
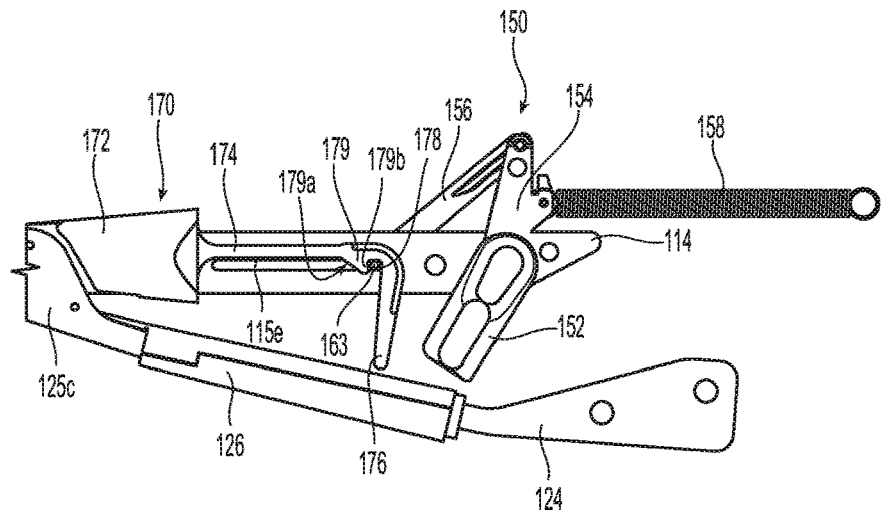
FIG. 14 is a side view of a proximal portion of the forceps of FIG. 1 with portions removed to illustrate a knife lockout of the forceps.

Turning to FIGS. 1, 2A, and 14, knife lockout 170 works in conjunction with shaft members 110, 120 to inhibit deployment of knife 140 prior to shaft members 110, 120 reaching a sufficiently-approximated position corresponding to a sufficiently-closed position of jaw members 210, 220. Knife lockout 170 includes a body 172 that is disposed about a portion of the inner frame 114 of shaft member 110 and forms a portion of outer housing 116 of shaft member 110. More specifically, as shown in FIG. 1, body 172 of knife lockout 170 defines a complementarily-shaped abutting surface with the abutting surface of the adjacent other component(s) of housing 116 such that housing 116 defines a substantially continuous outer surface. Body 172 extends at least partially within U-shaped distal clevis portion 125c of shaft member 110 to inhibit excess lateral play therebetween, as noted above.

Referring to FIG. 14, knife lockout 170 further includes a cantilever arm 174 extending proximally from body 172. Cantilever arm 174 and body 172 may be integrally formed, e.g., via injection molding, or may be attached in any other suitable fashion. Cantilever arm 174 extends along inner frame 114 of shaft member 110 on an opposite side of inner frame 114 as compared to second linkage 156 of knife deployment mechanism 150. Cantilever arm 174 defines a relatively narrowed configuration to permit flexing of cantilever arm 174. A finger 176 integrally formed with cantilever arm 174 extends generally perpendicularly from a free end of cantilever arm 174 and through an opening defined in outer housing 116 of shaft member 110 towards shaft member 120. A nook 178 is defined at the junction of cantilever arm 174 and finger 176. A stop 179 protrudes from cantilever arm 174 in the vicinity of nook 178 and defines an angled distal wall 179a and a vertical proximal wall 179b that, together with cantilever arm 174 and finger 176, enclose a portion of nook 178.

With shaft members 110, 120 sufficiently spaced-apart from one another, finger 176 of knife lockout 170 is spaced-apart from outer housing 126 of shaft member 120 such that cantilever arm 174 is disposed in its at-rest position. In the at-rest position, cantilever arm 174 extends along and in generally parallel orientation relative to longitudinal slot 115e of inner frame 114 of shaft member 110. Further, nook 178 is disposed at the proximal end of longitudinal slot 115e and receives the portion of pivot pin 163 that extends from second linkage 156 through longitudinal slot 115e therein. As such, vertical proximal wall 179b of stop 179 inhibits distal advancement of pivot pin 163 in the at-rest position of cantilever arm 174 and, accordingly, inhibits deployment of knife 140.

In order to disengage knife lockout 170 to permit deployment of knife 140, shaft members 110, 120 are sufficiently approximated such that a portion of outer housing 126 of shaft member 120 contacts finger 176 of knife lockout 170 and urges finger 176 further into housing 116 of shaft member 110. As finger 176 is urged further into housing 116, cantilever arm 174 is flexed such that nook 178 is withdrawn from about pivot pin 163 and vertical proximal wall 179b of stop 179 is removed from the path of pivot pin 163. Once this has been achieved, knife deployment mechanism 150 may be actuated, as detailed above, to advance pivot pin 163 distally through slot 115e to deploy knife 140 from the retracted position towards the extended position.

Should shaft members 110, 120 be moved apart from one another sufficiently such that shaft member 120 no longer urges finger 176 to flex cantilever arm 174, cantilever arm 174 is resiliently returned to its at-rest position. If knife 140 is disposed in the retracted position at this point, nook 178 is returned to surrounding engagement about pivot pin 163. However, if knife 140 is disposed in the deployed position or a partially-deployed position, the return of cantilever arm 174 to its at-rest position does not re-capture pivot pin 163. Rather, upon subsequent return of knife 140 to the retracted position, pivot pin 163 is moved proximally and into contact with angled distal wall 179a of stop 179, camming therealong and urging cantilever arm 174 to flex from the at-rest position sufficiently so as to enable pivot pin 163 to return to the proximal end of longitudinal slot 115e. Once pivot pin 163 reaches this position, cantilever arm 174 is returned to the at-rest position and, as a result, nook 178 is returned to surrounding engagement about pivot pin 163, thereby locking-out knife 140 until shaft members 110, 120 are once again sufficiently approximated. The biasing force of biasing member 158 is sufficient to move pivot pin 163 proximally to deflect cantilever arm 174 and reset knife lockout 170 as detailed above. As such, resetting of knife lockout 170 occurs automatically (if shaft members 110, 120 are sufficiently spaced-apart) upon return of knife 140 to the retracted position.

Figure 15:
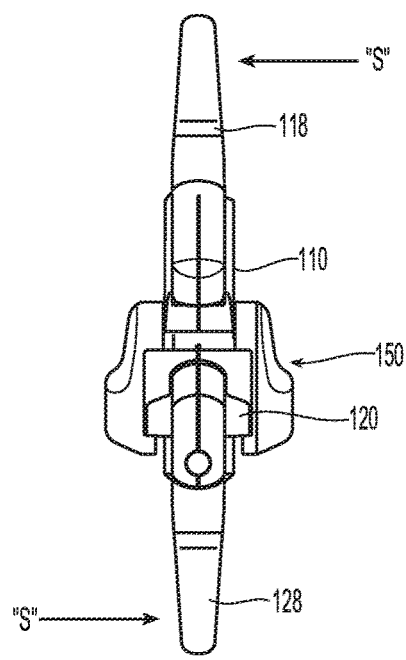
FIG. 15 is a rear view of the forceps of FIG. 1.

With reference to FIGS. 2A, 3B, 3A, 4A, and 15, the above-detailed structural support features of shaft members 110, 120 inhibit splaying of shaft members 110, 120 during use, e.g., in the directions of arrows "S" (FIG. 15). More specifically, reinforcing plate 115b of inner frame 114, enlarged body portion 125a of inner frame 124, support plates 166, 168 (that retain handles 118, 128), and the lockbox configuration of shaft members 110, 120 all add structural support to shaft members 110, 120 to inhibit splaying of shaft members 110, 120 during use. Further, the positioning of knife 140 within channel 115h between body plate 115a and reinforcing plate 115b inhibits splay of knife 140 during use.

Figure 16A:
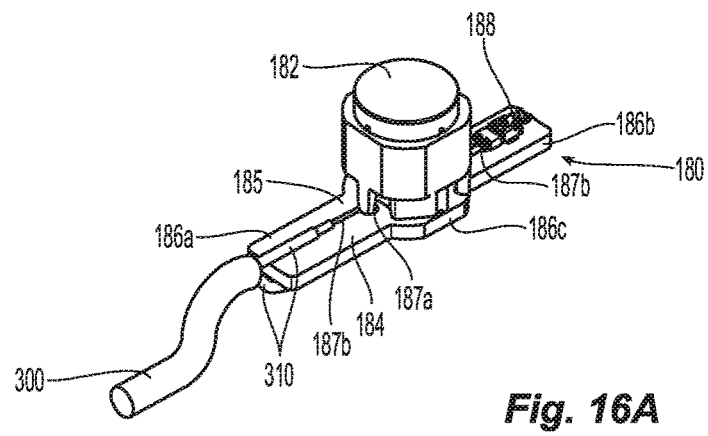
FIG. 16A is a top, perspective view of a switch assembly of the forceps of FIG. 1.
Figure 16B:
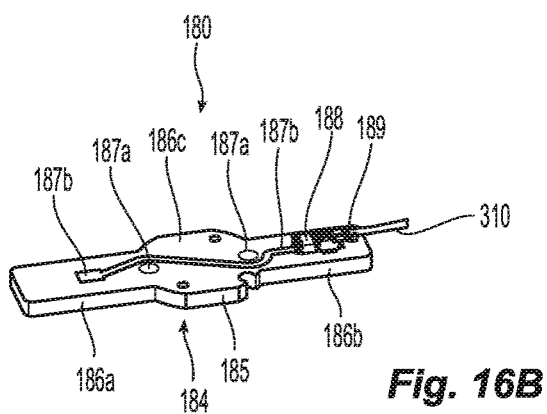
FIG. 16B is a bottom, perspective view of the switch assembly of FIG. 16A.

Turning to FIGS. 16A and 16B, switch assembly 180 is disposed on shaft member 120 and generally includes an activation button 182 and a Printed Circuit Board (PCB)

184. Activation button 182 includes a button housing 183*a* and a depressible button 183*b*. Depressible button 183*b* is configured to be contacted by the outer housing 116 of shaft member 110 upon sufficient approximation of shaft members 110, 120 so as to depress depressible button 183*b* and activate switch assembly 180. With additional reference to FIGS. 1-2B, as noted above, the position of shaft members 110, 120 wherein switch assembly 180 is activated, together with the flexion of inner frame 124, enable application of a particular jaw force, or jaw force within a particular range, to tissue grasped between jaw members 210, 220.

PCB 184 of switch assembly 180 includes a board body 185 defining a first end portion 186*a*, a second end portion 186*b*, and a central portion 186*c*. Central portion 186*c* of board body 185 is configured to receive activation button 182 thereon. More specifically, central portion 186*c* defines apertures 187*a* (or other suitable engagement features) to enable snap-fitting (or other suitable mechanical engagement) of activation button 182 thereon. Central portion 186*c* further defines circuit traces 187*b* such that, upon mechanical engagement of activation button 182 thereon, activation button 182 is also electrically coupled to PCB 184. This configuration facilitates assembly and reduces the possibility of improper connections. Circuit traces 187*b* extend from central portion 186*c* towards first end portion 186*a* of board body 185 on both the upper and lower faces of board body 185 to enable connection of a pair of lead wires 310 (only one of which is shown) of electrosurgical cable 300 thereto, e.g., via soldering. Circuit traces 187*b* also extend from central portion 186*c* towards second end portion 186*b* of board body 185 on both the upper and lower faces of board body 185. A quick-connect receptacle 188 is disposed on each of the upper and lower faces of body board 185 towards second end portion 186*b* thereof in electrical communication with circuit traces 187*b*. Quick-connect receptacles 188 facilitate engagement of lead wire receptacles 189 (only one of which is shown) therewith, thus facilitating coupling of the lead wires 310 of jaw members 210, 220 with switch assembly 180. More specifically, lead wire receptacles 189 are configured to slide into snap fit or other suitable engagement with quick-connect receptacles 188 to both mechanically engage lead wire receptacles 189 with PCB 184 and electrically couple the lead wires 310 of jaw members 210, 220 to corresponding portions of circuit traces 187*b*. As a result of the above-detailed configuration of switch assembly 180, activation of activation button 182 initiates the supply of energy from the energy source (not shown) to jaw members 210, 220 such that such energy may be conducted through tissue grasped between tissue-contacting plates 214, 224 of jaw members 210, 220 to treat tissue (see FIGS. 3A-4B).

Referring to FIGS. 17A-17H, the assembly of forceps 100 is detailed. In detailing the assembly of forceps 100 hereinbelow, additional structural features and functional benefits of forceps 100 may be described and/or become apparent. Accordingly, despite being described in connection with the assembly of forceps 100, the features of forceps 100 detailed herein (above or below) are not limited to assembly in the manner detailed below. Likewise, the advantageous order and manner of assembly of the components of forceps 100 as detailed below is not limited to use with the particular features of the various components of forceps 100 detailed above or otherwise herein.

Figure 17A:
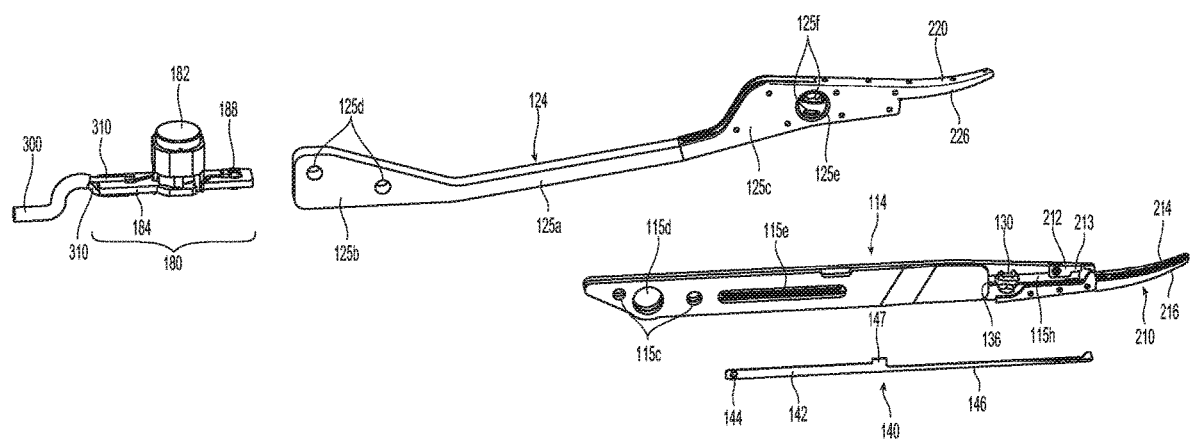
FIGS. 17A-17H illustrate assembly of the forceps of FIG. 1 in accordance with the present disclosure.
Figure 17B:
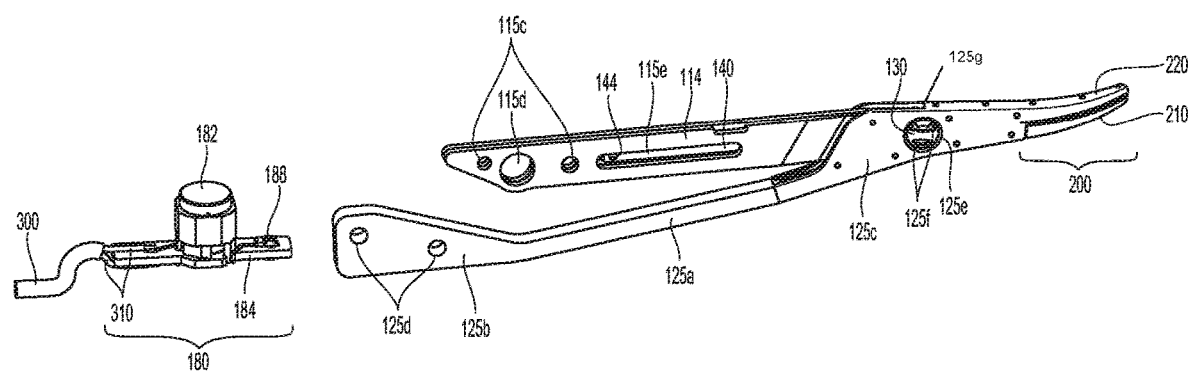

With initial reference to FIGS. 17A and 17B, inner frames 114, 124 of shaft members 110, 120 are pre-assembled with the respective jaw members 210, 220 thereon, as detailed above. Switch assembly 180 is also pre-assembled together with electrosurgical cable 300, as also detailed above. With inner frames 114, 124 pre-assembled with jaw members 210, 220, respectively, knife 140 may then be operably coupled to inner frame 114 of shaft member 110 such that knife 140 extends through longitudinal channel 115*h* of inner frame 114 and aperture 144 of knife 140 is aligned with longitudinal slot 115*e* of inner frame 114. Thereafter, shaft members 110, 120 are aligned to enable pivot member 130 to be inserted through aperture 125*e* of distal clevis portion 125*c* of inner frame 124, pivot aperture 115*f* of body plate 115*a* of inner frame 114, and into keyed aperture(s) 125*f* defined through the other side wall of distal clevis portion 125*c*. Upon such positioning, slot 136 of pivot member 130 receives a portion of knife 140. Body portion 132 of pivot member 130 may be welded, e.g., via laser welding, to the portion of the side wall of distal clevis portion 125*c* that surrounds keyed aperture(s) 125*f* at this point or later on during the assembly process. Location recess 134' of cap 134 of pivot member 130 (see FIG. 5C) is utilized during welding of pivot member 130 to distal clevis portion 125*c*, obviating the need to utilize a vision system to enable precise welding. Location recess 134' further serves as a "zero" position during component assembly, welding (as mentioned above in addition to other welding) and other fixation, and testing, e.g., jaw force testing, jaw gap testing, and electrical testing.

Figure 17C:
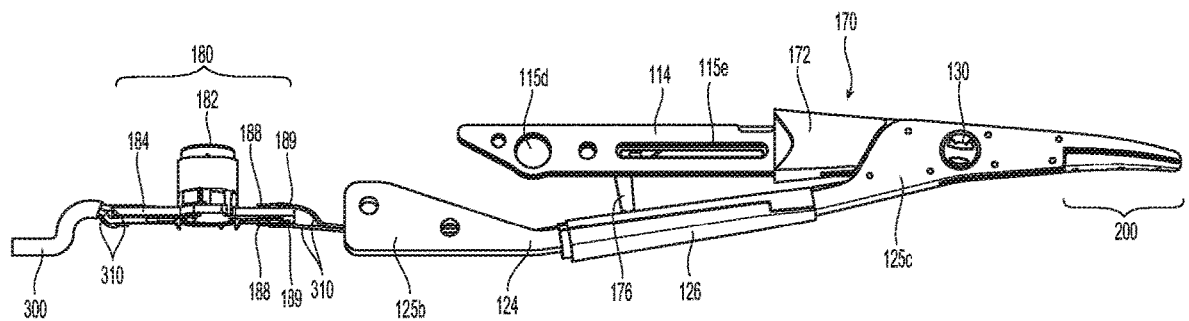

Turning to FIG. 17C, with inner frames 114, 124 of shaft members 110, 120 operably coupled to one another via pivot member 130 and with knife 140 operably coupled to inner frame 114, a portion of outer housing 126 of shaft member 120 is positioned on inner frame 124 and the lead wires 310 of jaw members 210, 220 are routed therethrough. Once routed through the portion of outer housing 126 installed on inner frame 124, the lead wires 310 of jaw members 210, 220 are operably coupled to switch assembly 180 via connection of lead wire receptacles 189 with quick-connect receptacles 188 of switch assembly 180, thereby electrically coupling jaw members 210, 220 with switch assembly 180 and electrosurgical cable 300. Additionally, at this point, knife lockout 170 is installed on inner frame 114 of shaft member 110.

Figure 17D:
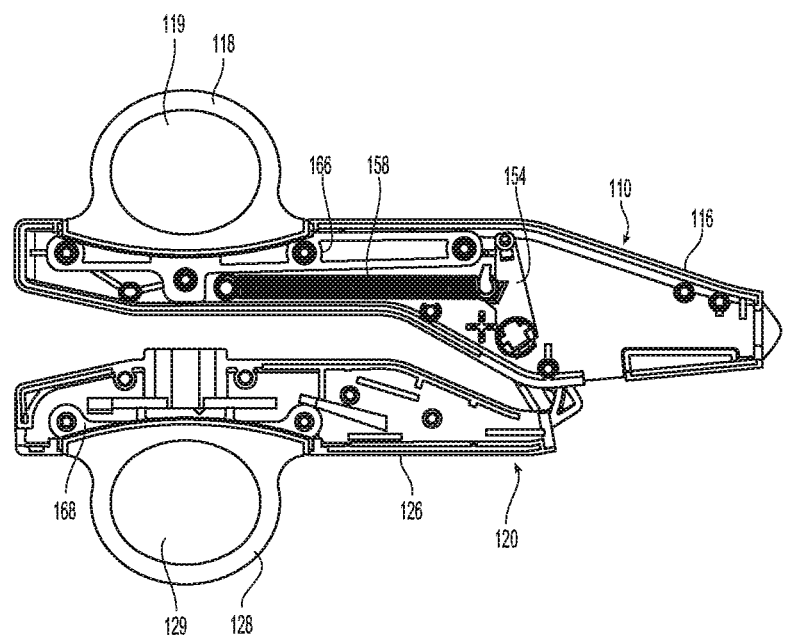

With reference to FIG. 17D, handles 118, 128 are engaged within first half-housing portions of outer housings 116, 126 of shaft members 110, 120, respectively, although handles 118, 128 may alternatively be pre-assembled with the first half-housing portions of outer housing 116, 126. First linkage 154 of knife deployment mechanism 150 is then operably positioned such that one of the pivot bosses 161 thereof extends through a corresponding aperture defined through the first half-housing portion of outer housing 116. Thereafter, biasing member 158 is operably coupled between first linkage 154 and handle 118, as detailed above. The trigger 152 corresponding to the first half-housing portion of outer housing 116 is also engaged about the portion of the pivot boss 161 that extends outwardly from the first half-housing portion of outer housing 116.

Figure 17E:
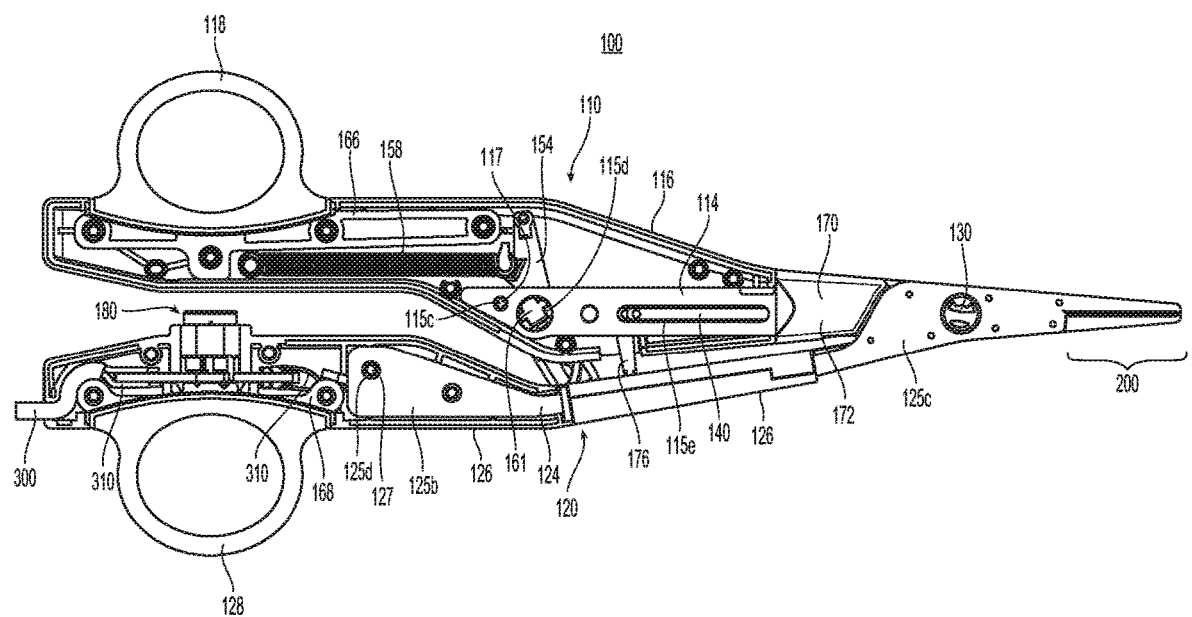

Referring to FIG. 17E, the subassembly of FIG. 17C and the subassembly of FIG. 17D are combined. More specifically, inner frames 114, 124 are operable engaged within the respective first half-housing portions of outer housing 116, 126. Further, switch assembly 180 and the distal end of electrosurgical cable 300 are seated within the first half-housing portion of outer housing 126 of shaft member 120.

Figure 17F:
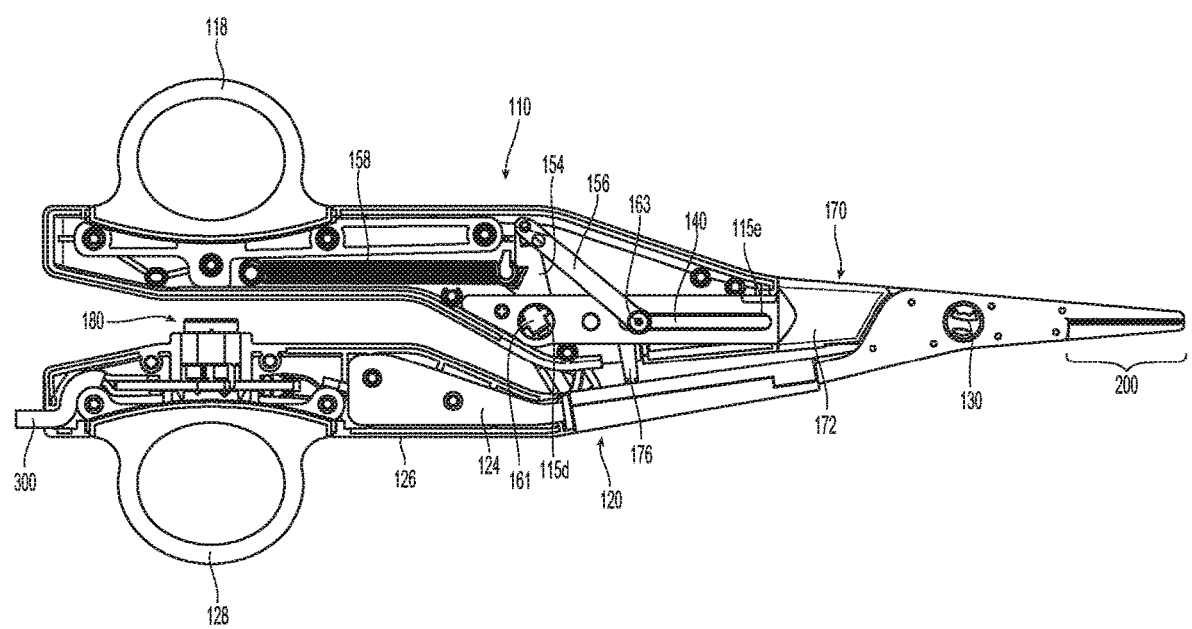
Figure 17G:
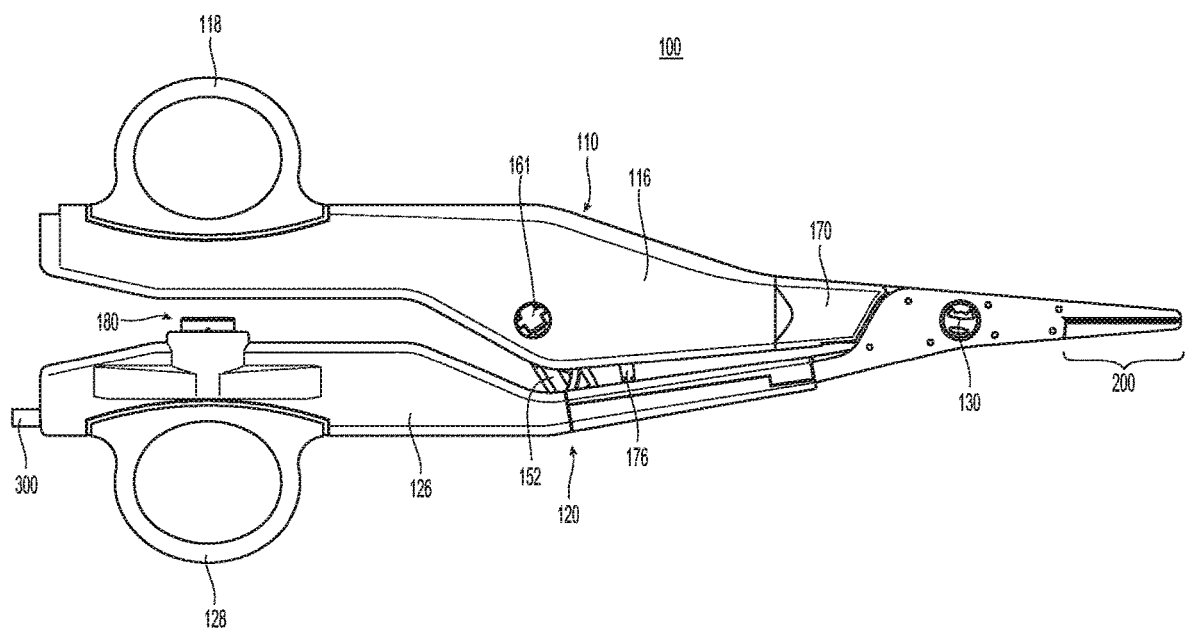

Turning to FIG. 17F, once the subassemblies of FIGS. 17C and 17D are combined as noted above, second linkage 156 of knife deployment assembly 150 is engaged to first linkage 154 and knife 140 (through inner frame 114 of shaft member 110). With the internal components of forceps 100 in place, the second half-housing portions of outer housing 116, 126 are moved into place to fully form outer housings 116, 126 and enclose the internal components therein, as illustrated in FIG. 17G. Finally, as shown in FIG. 17H, the other trigger 152 of knife deployment mechanism 150 is engaged with the corresponding pivot boss 161 of first linkage 154 on the second half-housing side of outer housing 116 of shaft member 110.

Once assembly is completed, e.g., as detailed above, testing may be performed to ensure proper operation of forceps 100. Such testing may include jaw force testing; testing using a gauge pin (not shown) to test the maximum jaw aperture between jaw members 210, 220 at the distal tips thereof; cut testing of the knife 140 using cut test media (not shown); testing of the gap distance between the tissue-contacting plates 214, 224 of jaw members 210, 220 (as set by the one or more stop members 215b and/or beak sections 218c of jaw members 210, 220) in the approximated position thereof at various positions along the lengths of jaw members 210, 220; and/or performing electrical continuity testing.

Figure 17H:
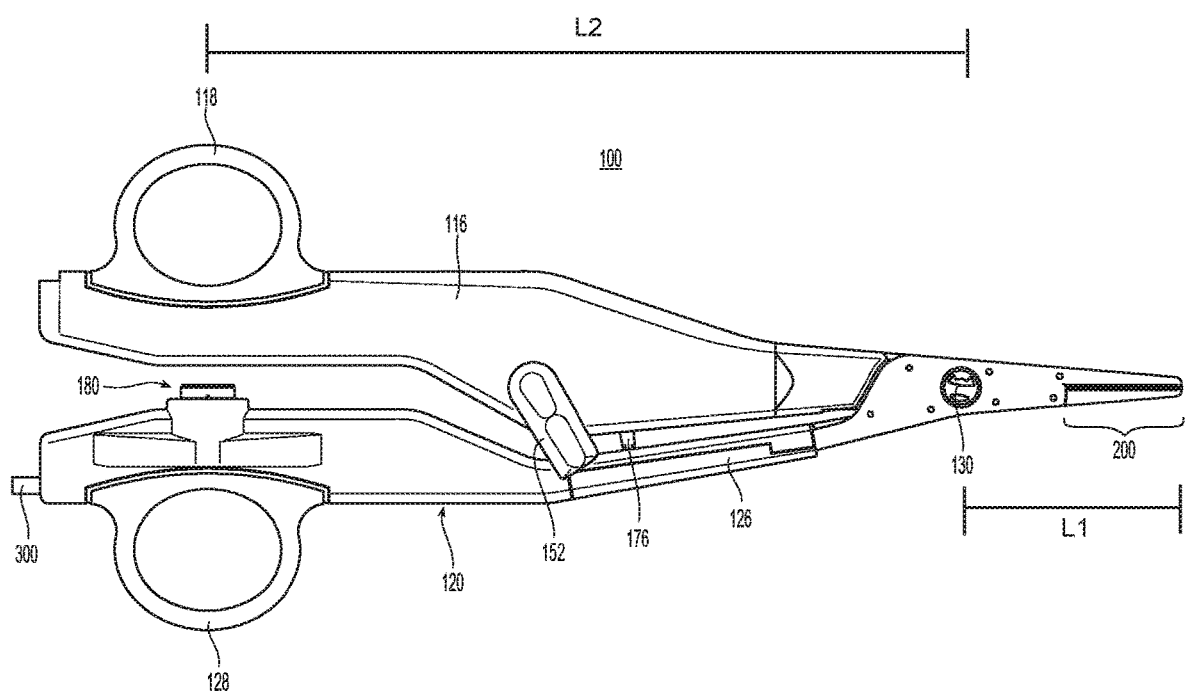

Referring to FIG. 17H, forceps 100, once fully assembled, defines a first length "L1" extending distally from the midpoint of pivot member 130 to the distal tip of jaw members 210, 220 (FIG. 1) of end effector assembly 200 and a second length "L2" extending proximally from the midpoint of pivot member 130 to the midpoint of handles 118, 128. A ratio L2:L1 of the second length to the first length is from about 2.0 to about 4.0 to provide the surgeon witan expected feel. More specifically, a ratio L2:L1 ranging from about 2.0 to about 4.0 has been found to correspond to an expected feel such that when a surgeon pivots handles 118, 128 towards or away from one another, jaw members 210, 220 (FIG. 1) are pivoted relative to one another an expected amount or close thereto. Ratios outside this range may require that the surgeon learn the device to achieve desired movement of the jaw members 210, 220 (FIG. 1), whereas forceps 100 provides an expected feel without the need for, or minimal, learning. As an example without limitation, length L1 may be about 4 cm and length L2 may be about 14 cm, thereby providing a ratio L2:L1 of 3.5.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:

first and second shaft members each including an inner frame, a jaw member secured to and extending distally from the inner frame, and an outer housing surrounding a portion of the inner frame, the jaw member of the first shaft member including a jaw support engaged with the inner frame of the first shaft member;

an insulative housing surrounding a portion of the jaw support and extending proximally about a portion of the inner frame of the first shaft member;

a pivot member pivotably coupling the inner frames of the first and second shaft members to one another such that pivoting of the first and second shaft members relative to one another between spaced-apart and approximated positions pivots the jaw members relative to one another between open and closed positions;

a knife selectively translatable through the first shaft member from a retracted position to an extended position wherein the knife extends at least partially between the jaw members;

a knife deployment mechanism operably coupled to the first shaft member, the knife deployment mechanism including at least one trigger and at least one linkage coupling the at least one trigger with the knife such that pivoting of the at least one trigger relative to the first shaft member translates the knife between the retracted and extended positions; and a knife lockout including a cantilever arm biased towards a locked position inhibiting distal translation of the knife, the cantilever arm movable upon approximation of the jaw members from the locked position to an unlocked position to permit distal translation of the knife, the knife lockout including a finger extending from the cantilever arm, the finger defining a nook including a proximal wall and a distal wall, wherein, in the locked position of the cantilever arm, a pivot pin of the knife is received between the proximal wall and the distal wall of the nook to prevent distal translation of the knife.

2. The electrosurgical forceps according to claim 1, wherein the knife lockout further includes a body, the body forming a portion of the outer housing of the first shaft member, the cantilever arm extending from the body within the outer housing of the first shaft member, and the finger extending from the cantilever arm externally of the outer housing of the first shaft member towards the second shaft member, wherein, in the approximated position of the first and second shaft members, the outer housing of the second shaft member is configured to contact the finger and urge the cantilever arm to the unlocked position permitting distal translation of the knife.

3. The electro surgical forceps according to claim 2, wherein the cantilever arm, the body, and the finger of the knife lockout are a single, monolithic component.

4. The electrosurgical forceps according to claim 1, wherein the pivot pin pivotably couples the at least one linkage of the knife deployment mechanism and the knife.

5. The electro surgical forceps according to claim 1, wherein the inner frame of the first shaft member includes a body plate, a reinforcing plate secured to the body plate, and a channel defined between the body plate and a reinforcing plate, and wherein the knife is slidably disposed within the channel.

6. The electrosurgical forceps according to claim 1, wherein the at least one linkage of the knife deployment mechanism includes a first linkage and a second linkage, the first linkage including at least one boss at a first end portion thereof, the at least one boss engaging the at least one trigger with the first linkage, the first linkage pivotably coupled to a first end portion of the second linkage at a second end portion of the first linkage, the second linkage pivotably coupled to the knife at a second end portion of the second linkage.

7. The electro surgical forceps according to claim 6, wherein the inner frame of the first shaft member defines an aperture, and wherein one of the at least one bosses of the first linkage extends through the aperture to pivotably couple the first linkage to the first shaft member.

8. The electro surgical forceps according to claim 6, wherein the first linkage is disposed on one side of the inner frame of the first shaft member, and wherein the second linkage is disposed on an opposite side of the inner frame of the first shaft member.

9. The electrosurgical forceps according to claim 8, wherein the cantilever arm of the knife lockout is disposed on a same side of the inner frame of the first shaft member as the first linkage.

10. The electrosurgical forceps according to claim 1, wherein the first and second shaft members each further include a handle engaged with a support plate, each support plate secured within the outer housing of the respective shaft member.

11. The electrosurgical forceps according to claim 10, wherein a biasing member is operably coupled between the support plate of the first shaft member and the knife deployment mechanism to bias the knife towards the retracted position.

12. The electrosurgical forceps according to claim 1, further comprising:
first and second lead wires extending through the second shaft member, the first and second lead wires electrically coupled to the first and second jaw members, respectively;
an electrosurgical cable coupled to the second shaft member and adapted to connect to a source of electrosurgical energy; and
a switch assembly disposed on the second shaft member, the switch assembly including an activation button and electrically coupling the first and second lead wires, the electrosurgical cable, and the activation button with one another such that actuation of the activation button supplies electrosurgical energy to the first and second jaw members.

13. The electrosurgical forceps according to claim 12, wherein in the approximated position of the first and second shaft members, the first shaft member is configured to actuate the activation button.

14. The electrosurgical forceps according to claim 12, wherein the switch assembly further includes a PCB having the activation button mounted on a central portion thereof, the electrosurgical cable electrically coupled to a first end portion thereof, and the first and second lead wires electrically coupled to a second end portion thereof, and the switch assembly further includes circuit traces defined on the PCB and electrically coupling the electrosurgical cable, the activation button, and the first and second lead wires with one another.

15. The electrosurgical forceps according to claim 14, wherein the switch assembly further includes at least one quick-connect receptacle disposed on the PCB at the second end portion thereof, the at least one quick-connect receptacle configured to facilitate electrical coupling of the first and second lead wires with the PCB.

16. The electrosurgical forceps according to claim 1, wherein an electrically-conductive tissue-contacting plate is disposed on the jaw support and partially surrounded by the insulative housing.

17. The electrosurgical forceps according to claim 16, wherein the jaw support is secured to the inner frame of the first shaft member and wherein the insulative housing is overmolded about the jaw support and the portion of the inner frame of the first shaft member.

18. The electrosurgical forceps according to claim 16, wherein a proximally-extending portion of the jaw support overlaps the inner frame of the first shaft member and defines a roof configured to receive a distal cutting portion of the knife in the retracted position of the knife.

19. The electrosurgical forceps according to claim 1, wherein the knife extends through a slot defined in the pivot member, and wherein the knife includes a stop shoulder inhibited from passing through the slot in the pivot member, the stop shoulder configured to abut the pivot member to define a distal-most position of the knife.

20. The electrosurgical forceps according to claim 1 wherein, in the approximated position of the first and second shaft members, the at least one trigger is fully disposed within a height dimension of the first and second shaft members such that the at least one trigger does not extend beyond the height dimension of the first and second shaft members.

* * * * *